United States Patent
Dyckman et al.

(10) Patent No.: US 11,998,537 B2
(45) Date of Patent: Jun. 4, 2024

(54) SUBSTITUTED INDOLE DIMER COMPOUNDS

(71) Applicant: BRISTOL-MYERS SQUIBB COMPANY, Princeton, NJ (US)

(72) Inventors: Alaric J. Dyckman, Lawrenceville, NJ (US); Brian K. Whiteley, Lebanon, NJ (US); John L. Gilmore, Yardley, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 637 days.

(21) Appl. No.: 17/287,735

(22) PCT Filed: Oct. 22, 2019

(86) PCT No.: PCT/US2019/057315
§ 371 (c)(1),
(2) Date: Apr. 22, 2021

(87) PCT Pub. No.: WO2020/086505
PCT Pub. Date: Apr. 30, 2020

(65) Prior Publication Data
US 2021/0393608 A1 Dec. 23, 2021

Related U.S. Application Data

(60) Provisional application No. 62/749,924, filed on Oct. 24, 2018.

(51) Int. Cl.
*A61K 31/4545* (2006.01)
*A61K 47/54* (2017.01)
*A61K 47/55* (2017.01)

(52) U.S. Cl.
CPC .......... *A61K 31/4545* (2013.01); *A61K 47/54* (2017.08); *A61K 47/55* (2017.08)

(58) Field of Classification Search
CPC ..... A61K 31/4545; A61K 47/54; A61K 47/55
See application file for complete search history.

(56) References Cited

U.S. PATENT DOCUMENTS

| | | | |
|---|---|---|---|
| 6,187,777 B1 | 2/2001 | Norman et al. | |
| 6,306,874 B1 | 10/2001 | Fraley et al. | |
| 6,867,200 B1 | 3/2005 | Allen et al. | |
| 7,410,975 B2 | 8/2008 | Lipford et al. | |
| 8,138,187 B2 | 3/2012 | Zemolka et al. | |
| 8,354,400 B2 | 1/2013 | Zheng et al. | |
| 9,126,996 B2 | 9/2015 | Lipford et al. | |
| 9,126,999 B2 | 9/2015 | Bolvin et al. | |
| 9,241,991 B2 | 1/2016 | Ji et al. | |
| 9,353,115 B2 | 5/2016 | Lipford et al. | |
| 9,376,398 B2 | 6/2016 | Hori et al. | |
| 9,428,495 B2 | 8/2016 | Carlson et al. | |
| 9,643,967 B2 | 5/2017 | Koul et al. | |
| 2004/0014802 A1 | 1/2004 | Dutruc-Rosset et al. | |
| 2006/0235037 A1 | 10/2006 | Purandare et al. | |
| 2010/0160314 A1 | 6/2010 | Lipford et al. | |
| 2010/0197657 A1 | 8/2010 | Chang et al. | |
| 2011/0015219 A1 | 1/2011 | Trawick et al. | |
| 2011/0071150 A1 | 3/2011 | Alam et al. | |
| 2011/0105427 A1 | 5/2011 | Daun et al. | |
| 2011/0183967 A1 | 7/2011 | Zheng et al. | |
| 2011/0275631 A1 | 11/2011 | Abeywardane et al. | |
| 2013/0045986 A1 | 2/2013 | Nagarathnam et al. | |
| 2013/0324547 A1 | 12/2013 | Boivin et al. | |
| 2014/0066432 A1 | 3/2014 | Howbert et al. | |
| 2014/0088085 A1 | 3/2014 | Burgess et al. | |
| 2014/0242121 A1 | 8/2014 | Lipford et al. | |
| 2015/0214490 A1 | 7/2015 | Kim et al. | |

(Continued)

FOREIGN PATENT DOCUMENTS

| | | |
|---|---|---|
| EP | 2738172 A1 | 6/2014 |
| WO | 03057696 A1 | 7/2003 |

(Continued)

OTHER PUBLICATIONS

Shukla, N. M., et al. J. Med. Chem. 2012, 55, 1106-1116. (Year: 2012).*
Bobko, M. et al., "Synthesis of 2,5-disubstituted-3-cyanoindoles", Tetrahedron Letters, 53 (2012) 200-202.
International Preliminary Report on Patentability for No. PCT/US2019/057315, dated May 6, 2021.
Kawai, T., et al., "The Role of Pattern-Recognition Receptors in Innate Immunity: Update on Toll-like Receptors", Nature Immunol., 2011, 11, 373-384.
Kutchukian, Peter S. et al., "Chemistry Informer Libraries: a chemoinformatics enabled approach to evaluate and advance synthetic methods", Chemical Science, 2016, vol. 7, No. 4, pp. 2604-2613.
Amphier, M. et al., "Novel Small Molecule Inhibitors of TLR7 and TLR9: Mechanism of Action and Efficacy in Vivo", Mol Pharmacol, 2014, 85:429-440.
Patra, Mahesh Chandra, et al., "Recent Progress in the Development of Toll-like Receptor (TLR) antagonists", Exp. Opin. on Therapeutic Patents, 2016, vol. 26, No. 6, 719-730.

(Continued)

*Primary Examiner* — Eric Olson
*Assistant Examiner* — Samuel L Galster
(74) *Attorney, Agent, or Firm* — Gary Greenblatt

(57) ABSTRACT

Disclosed are compounds of Formula (I) Formula (I) N-oxides, or salts thereof, wherein $G_1$, $G_2$, L, $R_{1a}$, $R_{1b}$, $R_4$, $R_5$, n, m, x, and y are defined herein. Also disclosed are methods of using such compounds as inhibitors of signaling through Toll-like receptor 7, or 8, or 9, and pharmaceutical compositions comprising such compounds. These compounds are useful in treating inflammatory and autoimmune diseases.

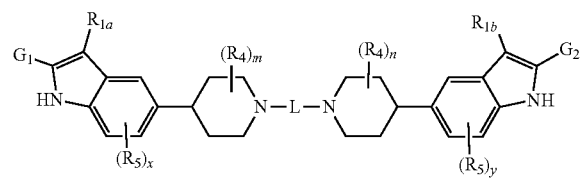

8 Claims, No Drawings

(56) References Cited

U.S. PATENT DOCUMENTS

| | | |
|---|---|---|
| 2015/0231142 A1 | 8/2015 | Van Goor et al. |
| 2017/0008885 A1 | 1/2017 | Koul et al. |
| 2017/0273983 A1 | 9/2017 | Ding et al. |
| 2018/0000790 A1 | 1/2018 | Dyckman et al. |

FOREIGN PATENT DOCUMENTS

| | | |
|---|---|---|
| WO | 2006113458 A1 | 10/2006 |
| WO | 2007000241 A1 | 1/2007 |
| WO | 2007115306 A2 | 10/2007 |
| WO | 2008065198 A1 | 6/2008 |
| WO | 2008152471 A1 | 12/2008 |
| WO | 2009030996 A1 | 3/2009 |
| WO | 2010149769 A1 | 12/2010 |
| WO | 2013010904 A1 | 1/2013 |
| WO | 2013181579 A2 | 12/2013 |
| WO | 2015088045 A1 | 6/2015 |
| WO | 2016029077 A1 | 2/2016 |
| WO | 2018005586 A1 | 1/2018 |
| WO | 2018026620 A1 | 2/2018 |
| WO | 2018049089 A1 | 3/2018 |
| WO | 2019126113 A1 | 6/2019 |

OTHER PUBLICATIONS

Roy, et al., "Design and developmen of benzoxazole derivatives with toll-like receptor 9 antagonism", Eur J Med Chem, 2017, vol. 134, 334-347.

Sims, et al., "The IL-1 Family: Regulators of Immunity", Nature Rev. Immunol., 2010, 10, 89-102.

Witherington, Jason, etl., "6-Heteroaryl-pyrazolo[3,4-b]pyridines: Potent and Selective Inhibitors of Glycogen Synthase Kinase-3 (GSK-3)", Bioorganic & Medicinal Chemistry Letters, 2003, 13, pp. 3059-3062.

\* cited by examiner

SUBSTITUTED INDOLE DIMER COMPOUNDS

CROSS-REFERENCE TO RELATED APPLICATIONS

This application is a national phase application under 35 U.S.C. § 371 of International Patent Application No. PCT/US2019/057315, filed Oct. 22, 2019, U.S. Provisional Application Ser. No. 62/749,924, filed Oct. 24, 2018, the contents of which are specifically incorporated fully herein by reference.

DESCRIPTION

The present invention generally relates to substituted indole dimer compounds useful as inhibitors of signaling through Toll-like receptor 7, 8, or 9 (TLR7, TLR8, TLR9) or combinations thereof. Provided herein are substituted indole dimer compounds, compositions comprising such compounds, and methods of their use. The invention further pertains to pharmaceutical compositions containing at least one compound according to the invention that are useful for the treatment of conditions related to TLR modulation, such as inflammatory and autoimmune diseases, and methods of inhibiting the activity of TLRs in a mammal.

Toll/IL-1 receptor family members are important regulators of inflammation and host resistance. The Toll-like receptor family recognizes molecular patterns derived from infectious organisms including bacteria, fungi, parasites, and viruses (reviewed in Kawai, T. et al., *Nature Immunol.*, 11:373-384 (2010)). Ligand binding to the receptor induces dimerization and recruitment of adaptor molecules to a conserved cytoplasmic motif in the receptor termed the Toll/IL-1 receptor (TIR) domain with the exception of TLR3, all TLRs recruit the adaptor molecule MyD88. The IL-1 receptor family also contains a cytoplasmic TIR motif and recruits MyD88 upon ligand binding (reviewed in Sims, J. E. et al., *Nature Rev. Immunol.*, 10:89-102 (2010)).

Toll-like receptors (TLRs) are a family of evolutionarily conserved, transmembrane innate immune receptors that participate in the first-line defense. As pattern recognition receptors, the TLRs protect against foreign molecules, activated by pathogen associated molecular patterns (PAMPs), or from damaged tissue, activated by danger associated molecular patterns (DAMPs). A total of 13 TLR family members have been identified, 10 in human, that span either the cell surface or the endosomal compartment. TLR7-9 are among the set that are endosomally located and respond to single-stranded RNA (TLR7 and TLR8) or unmethylated single-stranded DNA containing cytosine-phosphate-guanine (CpG) motifs (TLR9).

Activation of TLR7/8/9 can initiate a variety of inflammatory responses (cytokine production, B cell activation and IgG production, Type I interferon response). In the case of autoimmune disorders, the aberrant sustained activation of TLR7/8/9 leads to worsening of disease states. Whereas overexpression of TLR7 in mice has been shown to exacerbate autoimmune disease, knockout of TLR7 in mice was found to be protective against disease in lupus-prone MRL/lpr mice. Dual knockout of TLR7 and 9 showed further enhanced protection.

As numerous conditions may benefit by treatment involving modulation of cytokines, IFN production and B cell activity, it is immediately apparent that new compounds capable of modulating TLR7 and/or TLR8 and/or TLR9 and methods of using these compounds could provide substantial therapeutic benefits to a wide variety of patients.

The present invention relates to a new class of substituted indole dimer compounds found to be effective inhibitors of signaling through TLR7/8/9. These compounds are provided to be useful as pharmaceuticals with desirable stability, bioavailability, therapeutic index, and toxicity values that are important to their druggability.

SUMMARY OF THE INVENTION

The present invention provides compounds of Formula (I) that are useful as inhibitors of signaling through Toll-like receptor 7, 8, or 9 and are useful for the treatment of proliferative diseases, allergic diseases, autoimmune diseases and inflammatory diseases, or stereoisomers, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 7, 8, or 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating proliferative, metabolic, allergic, autoimmune and inflammatory diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with Toll-like receptor 7, 8, or 9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of Toll-like receptor 7, 8, or 9 related conditions, such as allergic disease, autoimmune diseases, inflammatory diseases, and proliferative diseases.

The compound of Formula (I) and compositions comprising the compounds of Formula (I) may be used in treating, preventing, or curing various Toll-like receptor 7, 8, or 9 related conditions. Pharmaceutical compositions comprising these compounds are useful for treating, preventing, or slowing the progression of diseases or disorders in a variety of therapeutic areas, such as allergic disease, autoimmune diseases, inflammatory diseases, and proliferative diseases.

These and other features of the invention will be set forth in expanded form as the disclosure continues.

DETAILED DESCRIPTION

The first aspect of the present invention provides at least one compound of Formula (I):

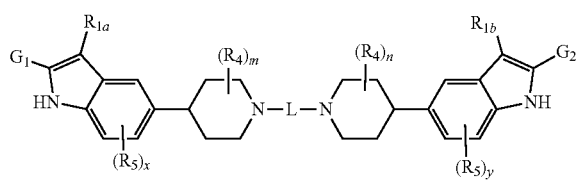
N-oxide, or a salt thereof, wherein:
L is —$(CH_2)_q$— or -$L_1$-$NR_xC(O)$—$(CH_2)_t$—$C(O)NR_x$-$L_2$-;
$L_1$ and $L_2$ are independently —$(CH_2)_{1-3}$—;
q is an integer in the range of 10 to 30;
t is an integer in the range of 2 to 24;
$G_1$ and $G_2$ are independently:
(i) 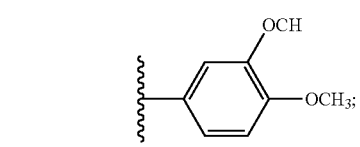
(ii) 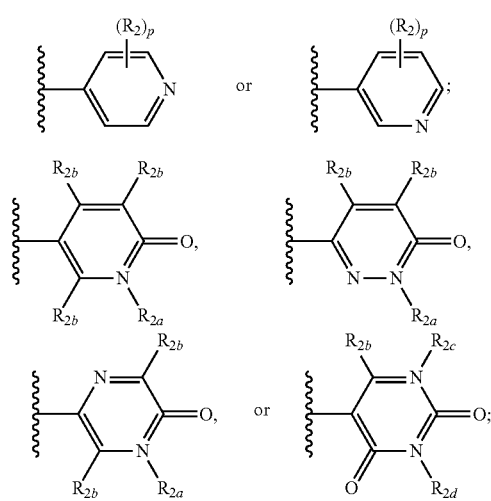
or
(iii)
(iv) a 9-membered heterocyclic ring selected from:
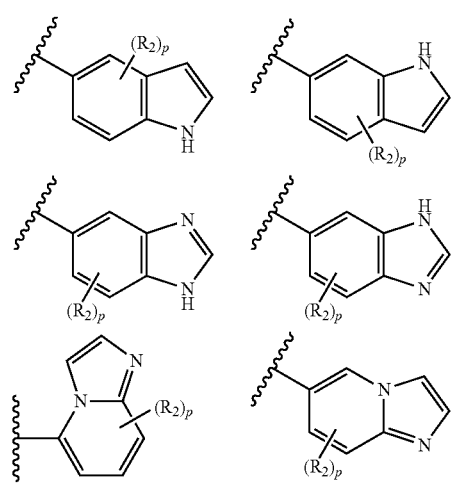
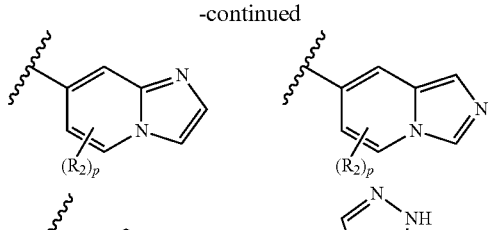
-continued
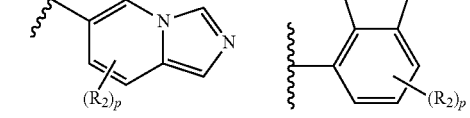
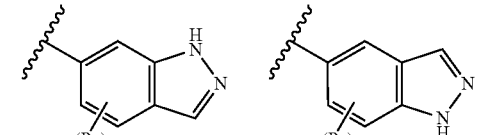
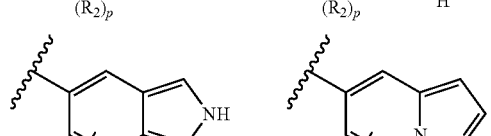
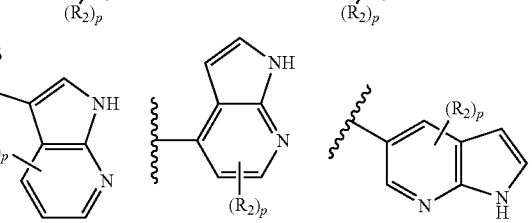
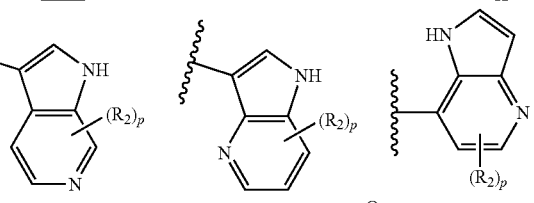
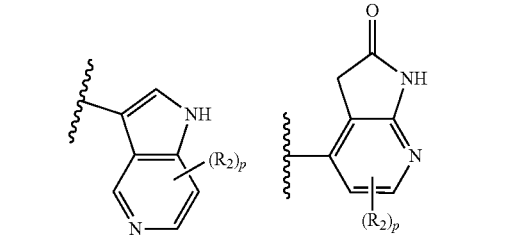
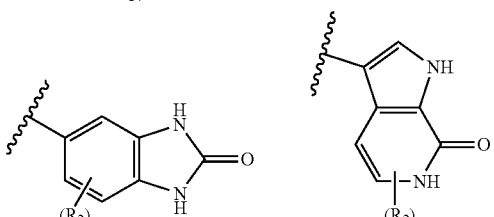
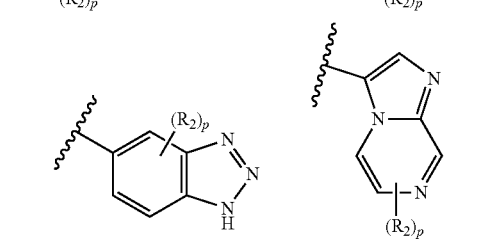

-continued
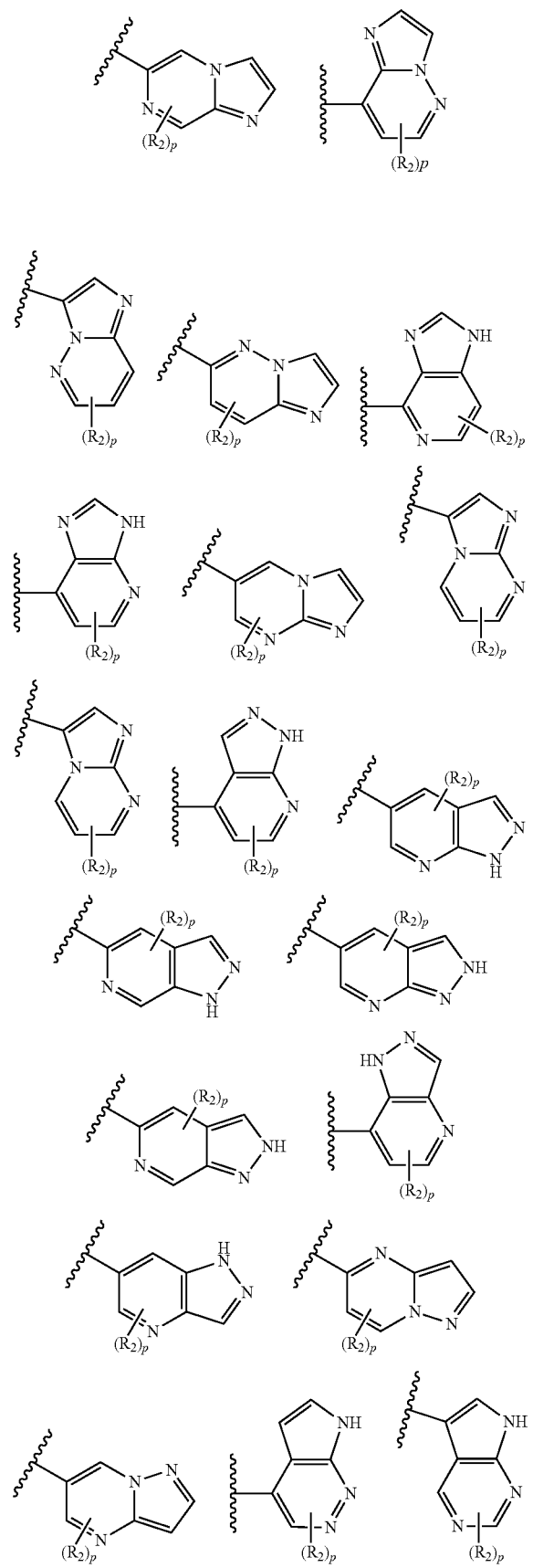
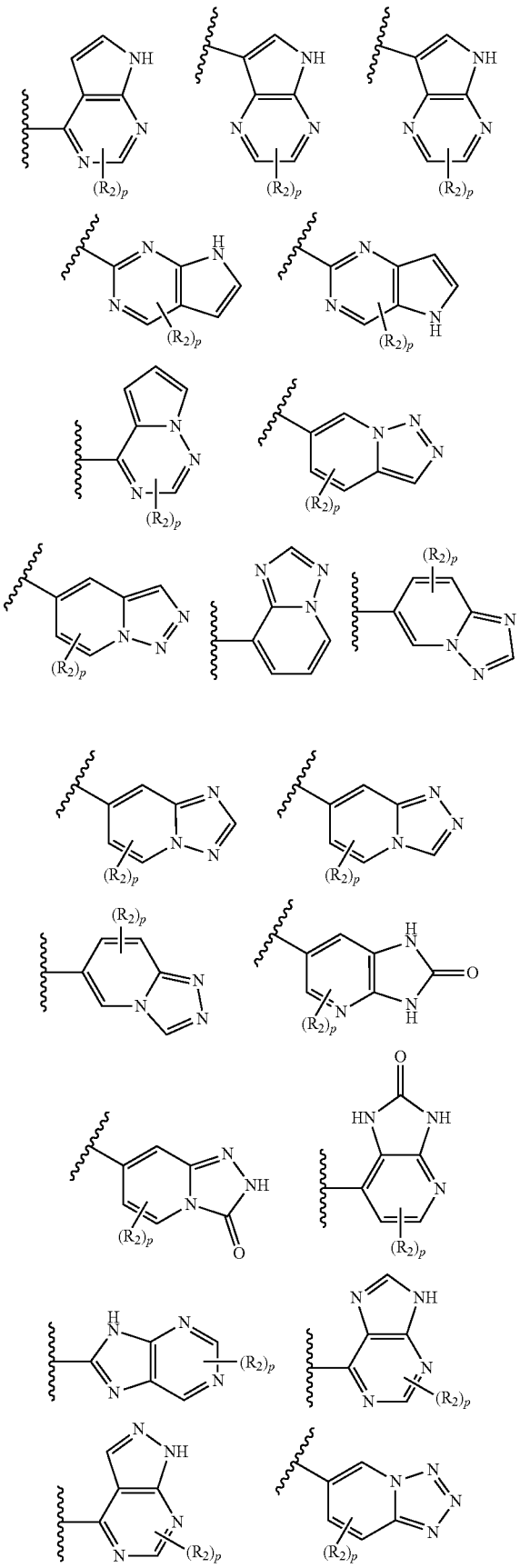

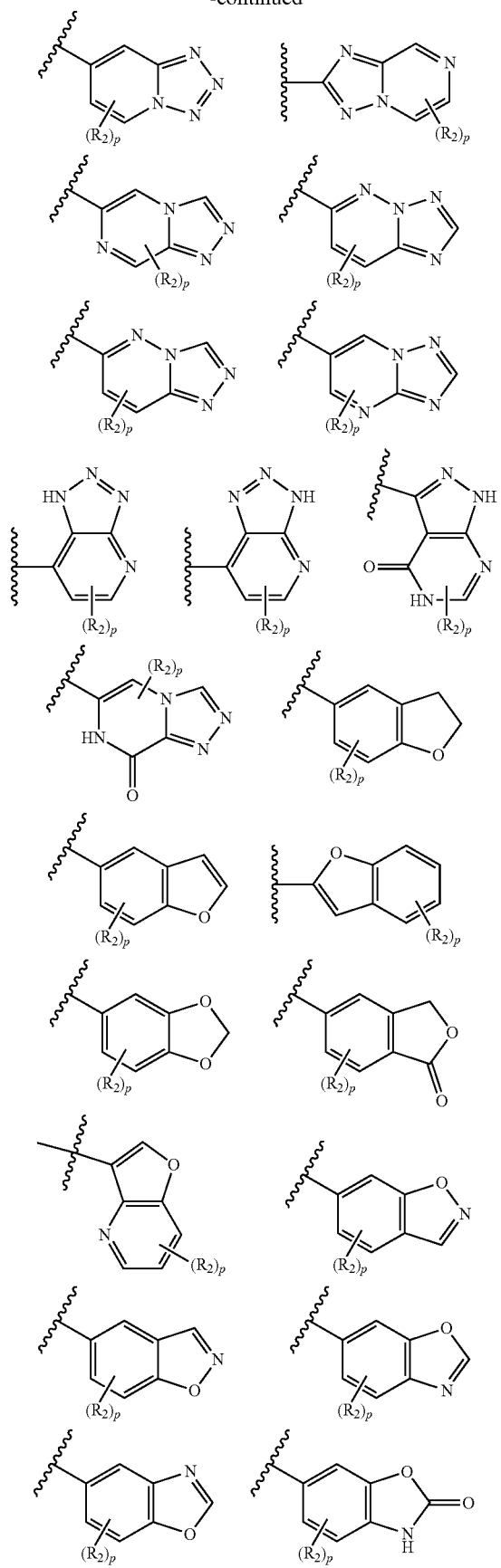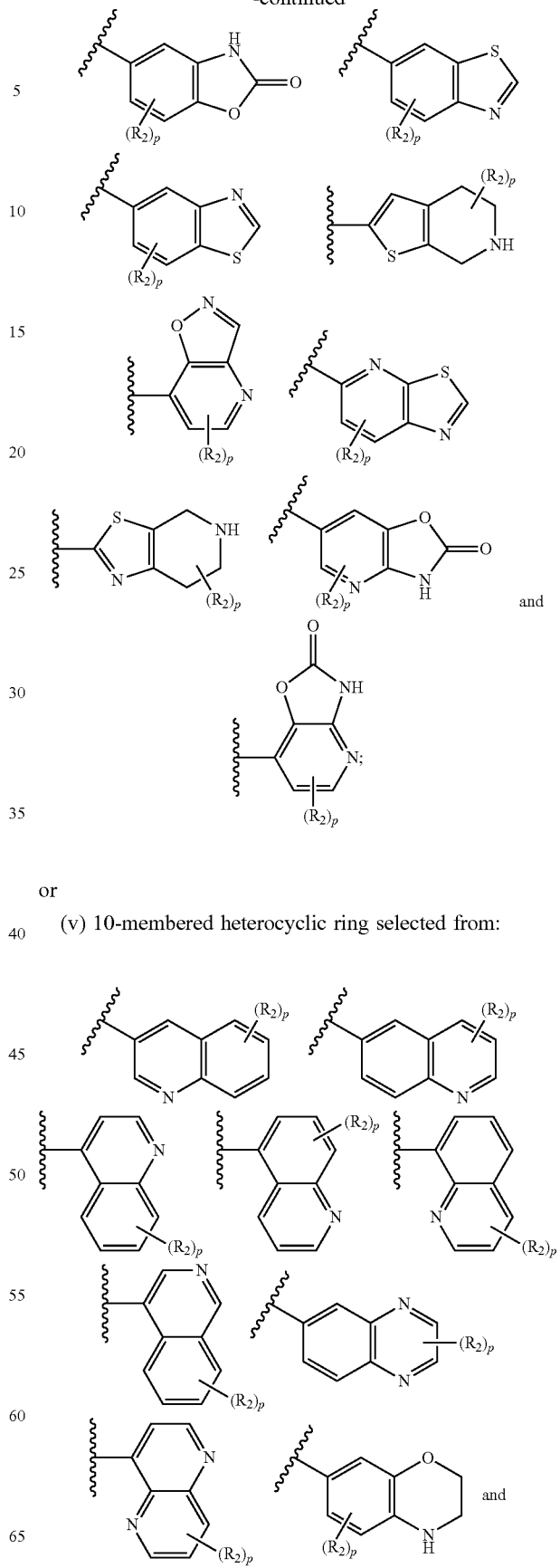
or
(v) 10-membered heterocyclic ring selected from:

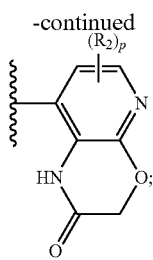

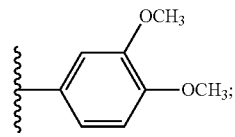 [SMILES: *c1ccc(OC)c(OC)c1]

$R_{1a}$ and $R_{1b}$ are independently H, Cl, —CN, $C_{1-4}$ alkyl, $C_{1-3}$ fluoroalkyl, $C_{1-3}$ hydroxy-fluoroalkyl, $C_{3-6}$ cycloalkyl, —CH$_2$($C_{3-6}$ cycloalkyl), —C(O)O($C_{1-3}$ alkyl), or tetrahydropyranyl;

each $R_2$ is independently halo, —CN, —OH, —NO$_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —O(CH$_2$)$_{1-2}$OH, —(CH$_2$)$_{0-4}$O($C_{1-4}$ alkyl), $C_{1-3}$ fluoroalkoxy, —(CH$_2$)$_{1-4}$O($C_{1-3}$ alkyl), —O(CH$_2$)$_{1-2}$OC(O)($C_{1-3}$ alkyl), —O(CH$_2$)$_{1-2}$NR$_x$R$_x$, —C(O)O($C_{1-3}$ alkyl), —(CH$_2$)$_{0-2}$C(O)NR$_y$R$_y$, —C(O)NR$_x$($C_{1-5}$ hydroxyalkyl), —C(O)NR$_x$($C_{2-6}$ alkoxyalkyl), —C(O)NR$_x$($C_{3-6}$ cycloalkyl), —NR$_y$R$_y$, —NR$_y$($C_{1-3}$ fluoroalkyl), —NR$_y$($C_{1-4}$ hydroxyalkyl), —NR$_x$CH$_2$(phenyl), —NR$_x$S(O)$_2$($C_{3-6}$ cycloalkyl), —NR$_x$C(O)($C_{1-3}$ alkyl), —NR$_x$CH$_2$($C_{3-6}$ cycloalkyl), —(CH$_2$)$_{0-2}$S(O)$_2$($C_{1-3}$ alkyl), —(CH$_2$)$_{0-2}$($C_{3-6}$ cycloalkyl), —(CH$_2$)$_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, —(CH$_2$)$_{0-4}$O($C_{1-3}$ alkyl), $C_{3-6}$ cycloalkyl, —(CH$_2$)$_{1-3}$C(O)NR$_x$R$_x$, —CH$_2$($C_{3-6}$ cycloalkyl), —CH$_2$(phenyl), tetrahydrofuranyl, tetrahydropyranyl, or phenyl;

each $R_{2b}$ is independently H, halo, —CN, —NR$_x$R$_x$, $C_{1-6}$ alkyl, $C_{1-3}$ fluoroalkyl, $C_{1-3}$ hydroxyalkyl, $C_{1-3}$ fluoroalkoxy, —(CH$_2$)$_{0-2}$O($C_{1-3}$ alkyl), —(CH$_2$)$_{0-3}$C(O)NR$_x$R$_x$, —(CH$_2$)$_{1-3}$($C_{3-6}$ cycloalkyl), —C(O)O($C_{1-3}$ alkyl), —C(O)NR$_x$($C_{1-3}$ alkyl), —CR$_x$=CR$_x$R$_x$, or —CR$_x$=CH($C_{3-6}$ cycloalkyl);

$R_{2c}$ is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_2$ is $R_{2b}$;

each $R_4$ is independently F, —OH, $C_{1-2}$ alkyl, or —OCH$_3$; or two $R_4$ attached to the same carbon atom form =O; or wherein when m or n is at least 2, two $R_4$, each attached to a different carbon atom adjacent to the nitrogen atom in a piperidinyl ring, can form a —CH$_2$CH$_2$— bridge;

each $R_5$ is independently F, Cl, —CN, $C_{1-3}$ alkyl, $C_{1-2}$ fluoroalkyl, or —OCH$_3$;

each $R_x$ is independently H or —CH$_3$;

each $R_y$ is independently H or $C_{1-6}$ alkyl;

m is zero, 1, 2, 3, or 4;

n is zero, 1, 2, 3, or 4;

each p is independently zero, 1, 2, 3, or 4;

x is zero, 1, or 2; and y is zero, 1, or 2.

One embodiment provides a compound of Formula (I) or a salt thereof wherein $G_1$ and $G_2$ are independently:

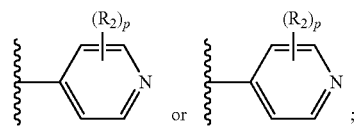

and L, $R_{1a}$, $R_{1b}$, $R_4$, $R_5$, m, n, x, and y are defined in the first aspect or the second aspect.

One embodiment provides a compound of Formula (I), N-oxide, or a salt thereof wherein $G_1$ and $G_2$ are independently:

and L, $R_{1a}$, $R_{1b}$, $R_2$, $R_4$, $R_5$, m, n, x, and y are defined in the first aspect.

One embodiment provides a compound of Formula (I) or a salt thereof wherein $G_1$ and $G_2$ are independently

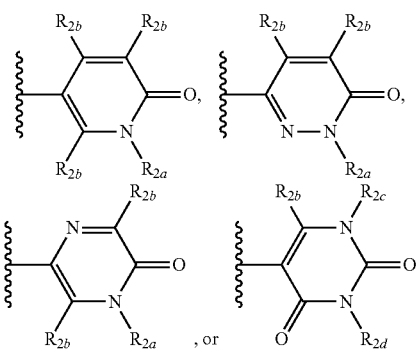

and L, $R_{1a}$, $R_{1b}$, $R_{2a}$, $R_{2b}$, $R_{2c}$, $R_{2d}$, $R_4$, $R_5$, m, n, x, and y are defined in the first aspect. Included in this embodiment are compounds in which $R_{2a}$ is $C_{1-4}$ alkyl, $C_{1-2}$ fluoroalkyl, $C_{1-4}$ hydroxyalkyl, —(CH$_2$)$_{1-3}$OCH$_3$, $C_{3-6}$ cycloalkyl, —CH$_2$C(O)NR$_x$R$_x$, —CH$_2$($C_{3-6}$ cycloalkyl), —CH$_2$(phenyl), tetrahydrofuranyl, or phenyl; and each $R_{2b}$ is independently H, F, Cl, —CN, —NR$_x$R$_x$, $C_{1-6}$ alkyl, $C_{1-2}$ fluoroalkyl, $C_{1-3}$ hydroxyalkyl, —(CH$_2$)$_{0-2}$O($C_{1-2}$ alkyl), —(CH$_2$)$_{0-2}$C(O)NR$_x$R$_x$, —(CH$_2$)$_{1-3}$(cyclopropyl), —C(O)O($C_{1-2}$ alkyl), —C(O)NR$_x$($C_{1-3}$ alkyl), —CR$_x$=CH$_2$, or —CH=CH($C_{3-6}$ cycloalkyl). Also included in this embodiment are compounds in which $R_{2a}$ is —CH$_3$; and each $R_{2b}$ is independently H, Cl, or —CH$_3$.

One embodiment provides a compound of Formula (I) or a salt thereof, wherein each of $G_1$ and $G_2$ is independently a 9-membered heterocyclic ring selected from:

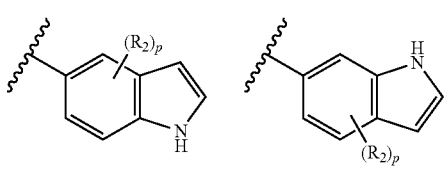

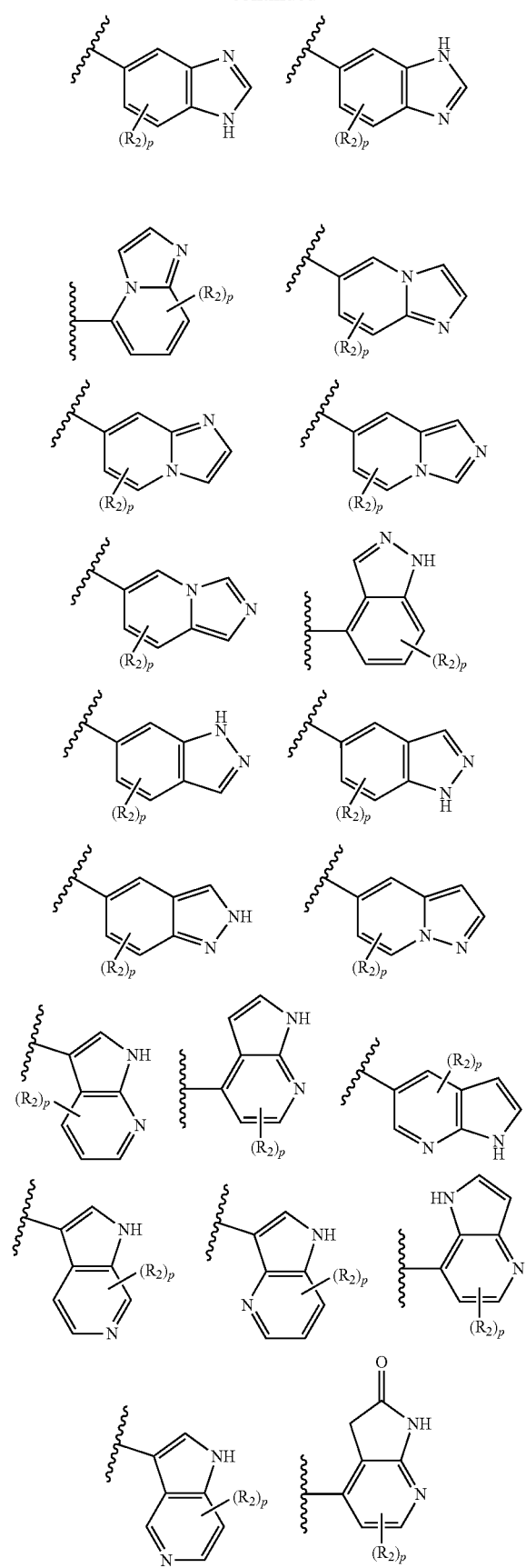
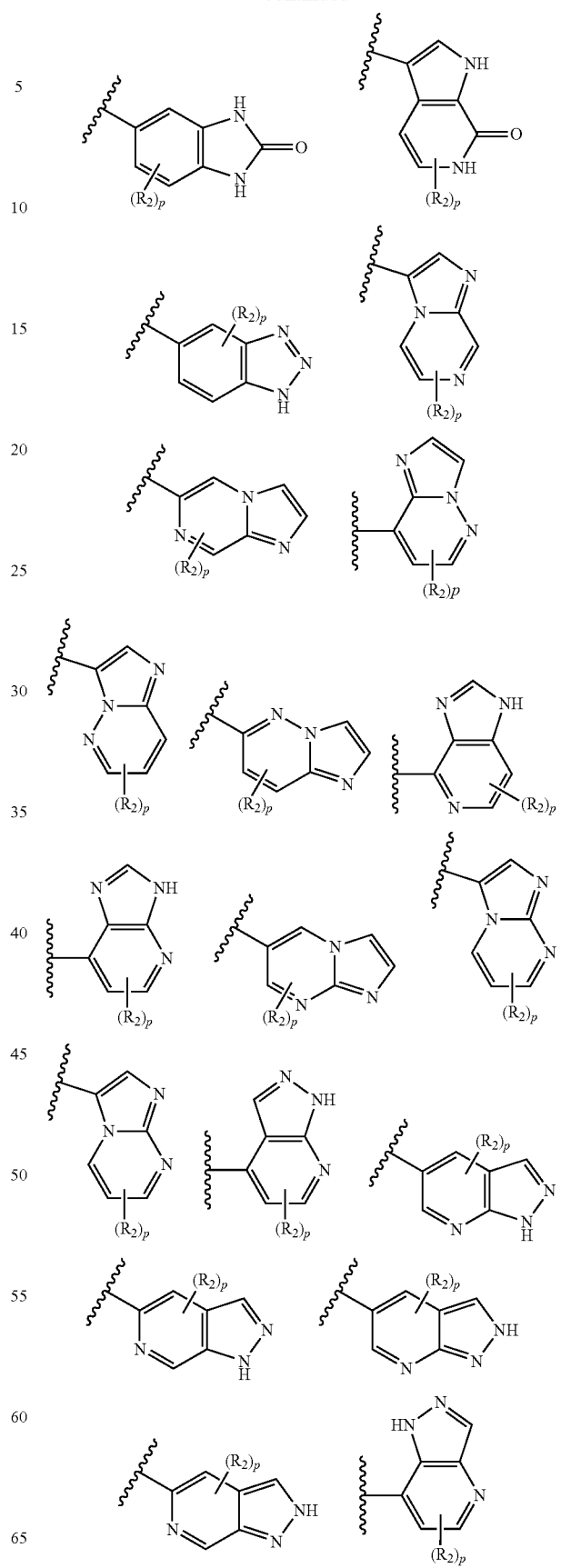

-continued
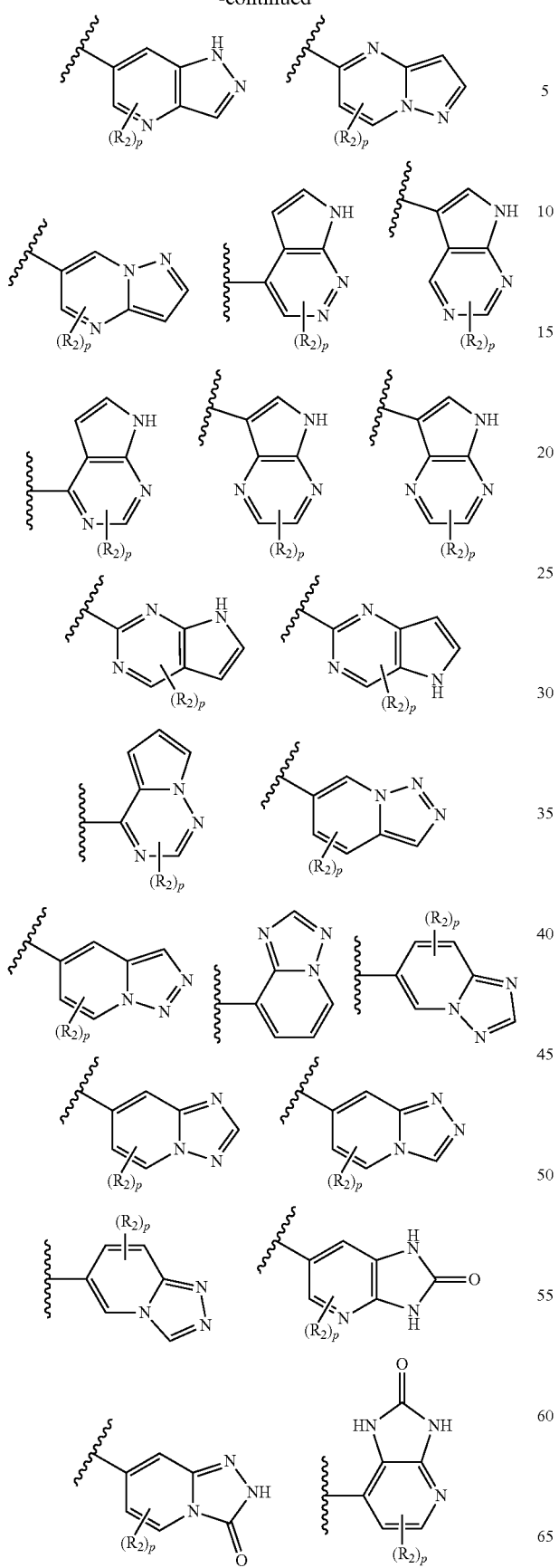
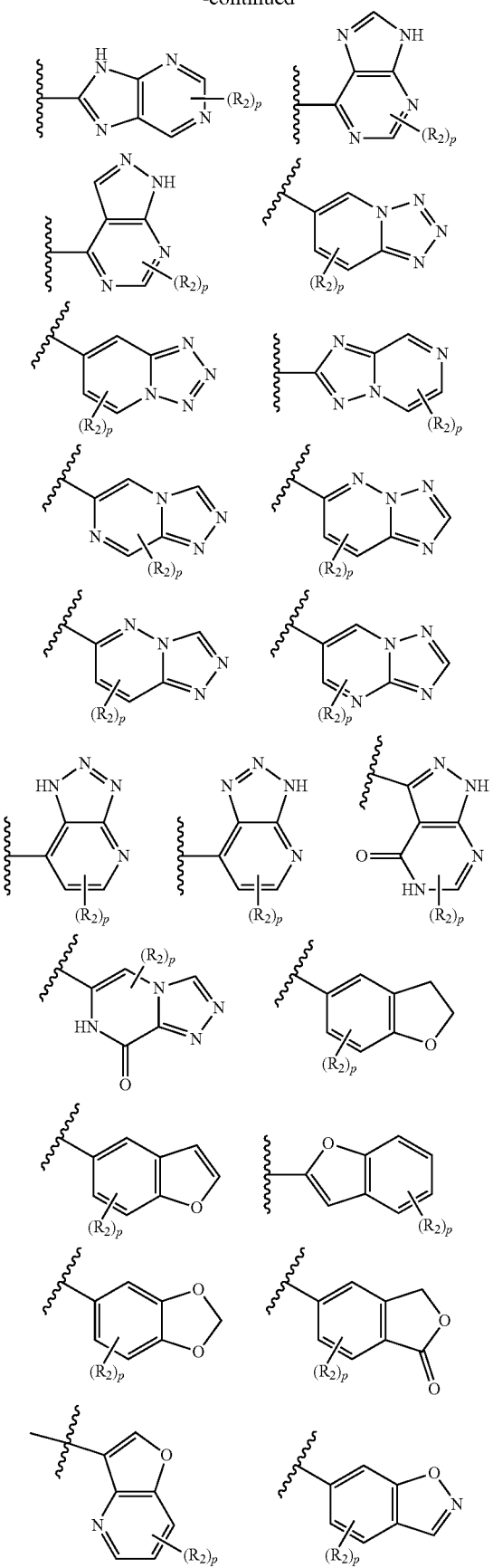

-continued

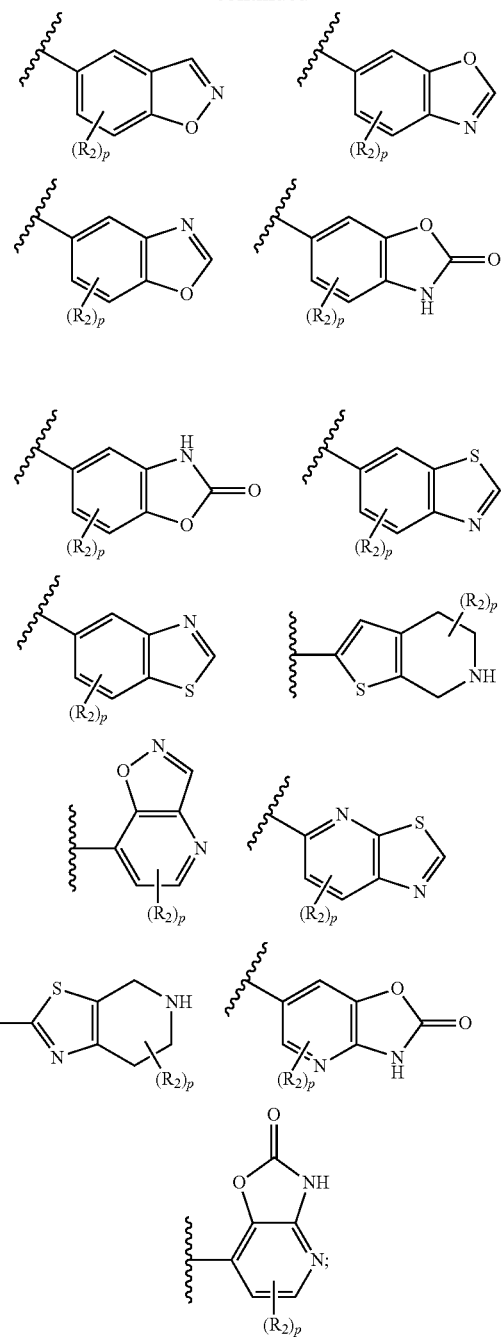

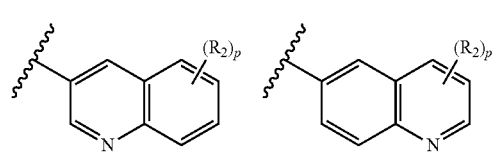

and L, $R_{1a}$, $R_{1b}$, $R_2$, $R_4$, $R_5$, m, n, n, p, x, and y are defined in the first aspect.

One embodiment provides a compound of Formula (I) or a salt thereof, wherein each of $G_1$ and $G_2$ is independently a 10-membered heterocyclic ring selected from:

-continued

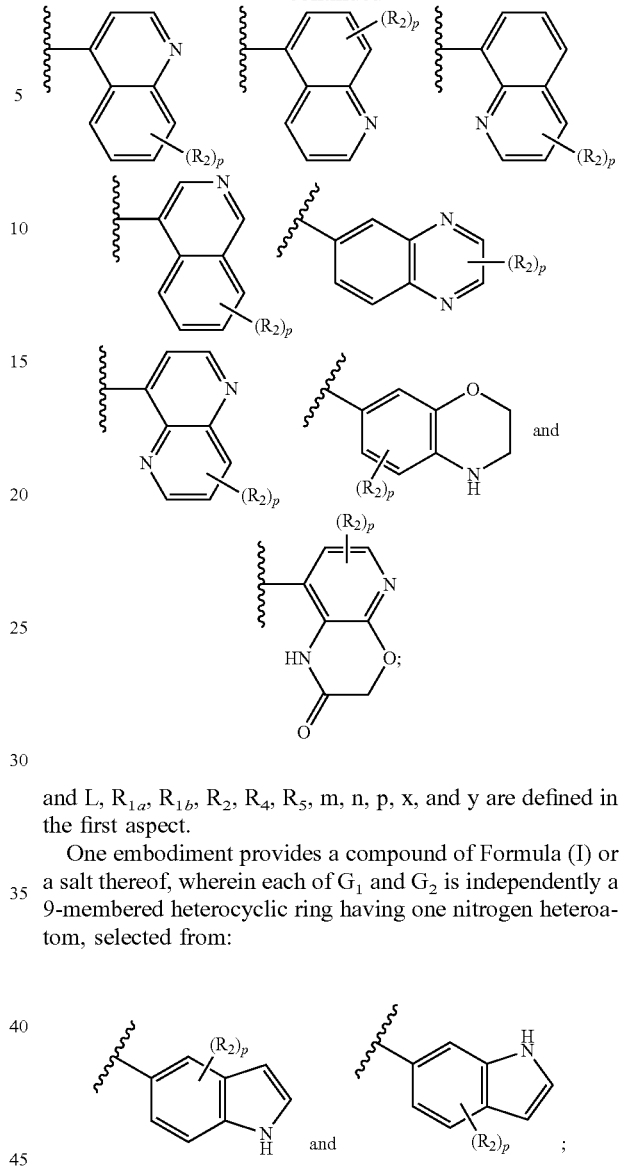

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having one nitrogen heteroatom, selected from:

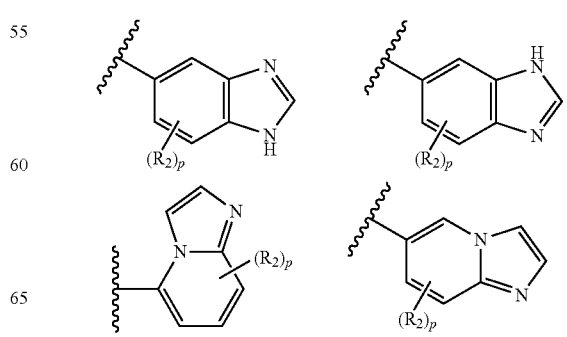

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having two nitrogen heteroatoms selected from:

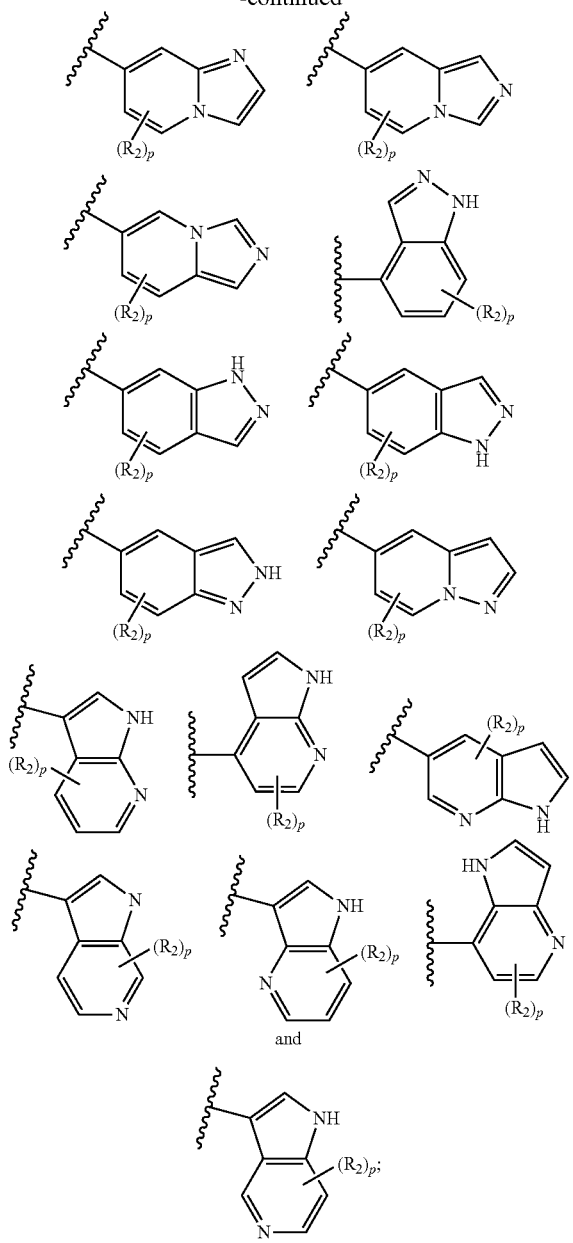

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having two nitrogen heteroatoms and is substituted with =O, selected from:

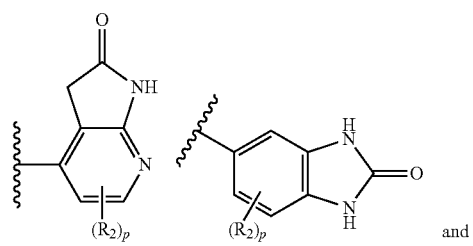

and

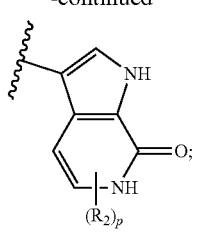

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having three nitrogen heteroatoms, selected from:

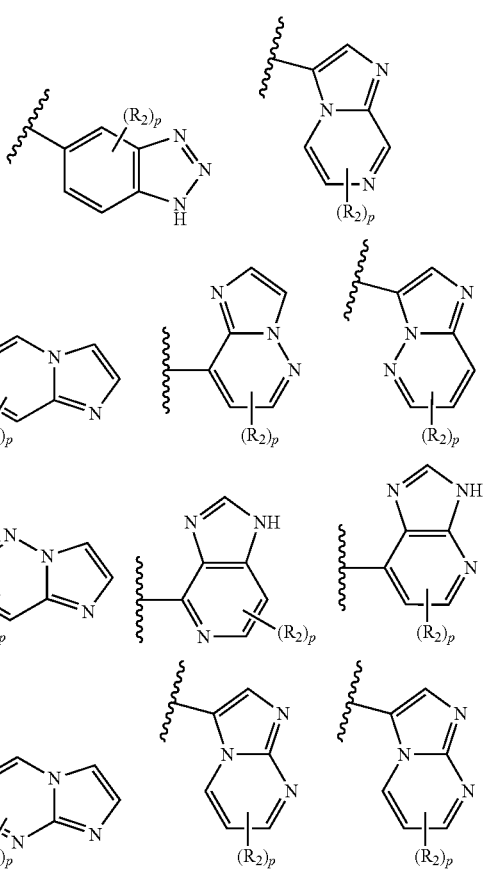

-continued

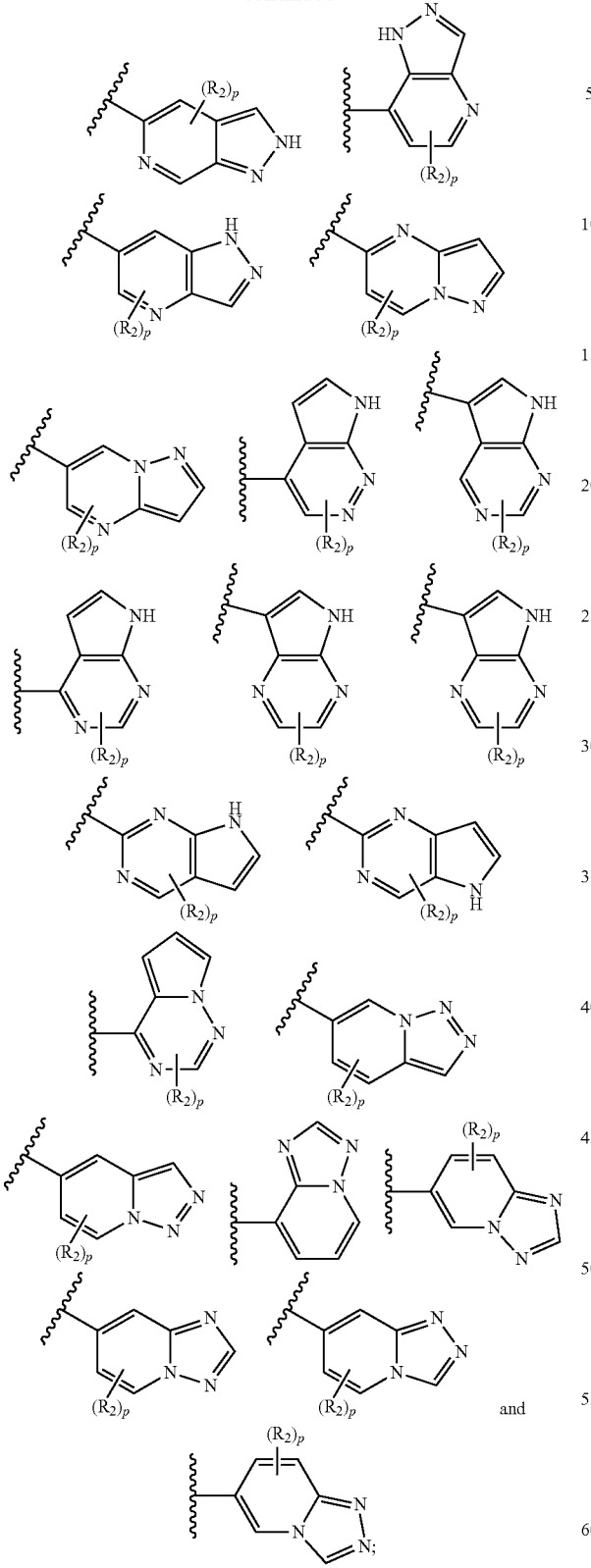

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having three nitrogen heteroatoms and is substituted with =O, selected from:

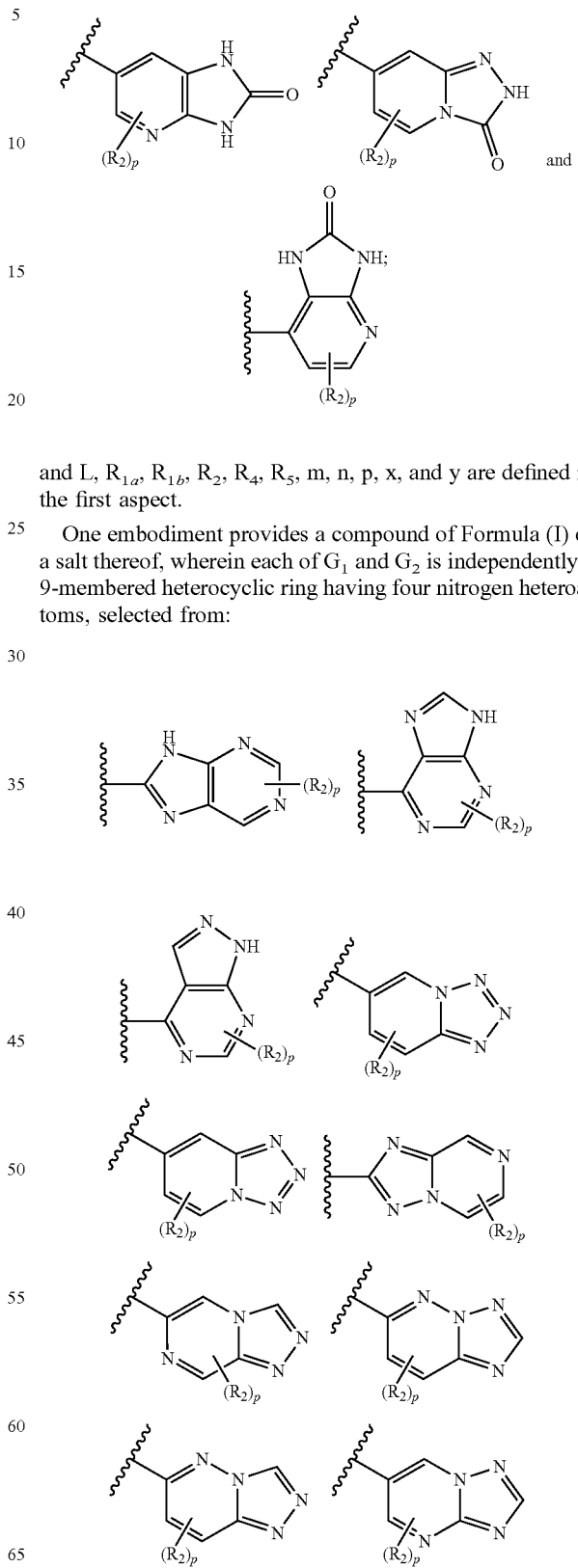

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having four nitrogen heteroatoms, selected from:

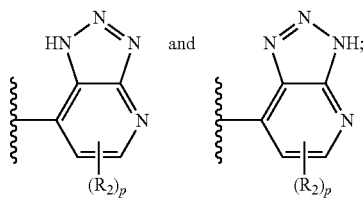

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having four nitrogen heteroatoms and is substituted with =O, selected from:

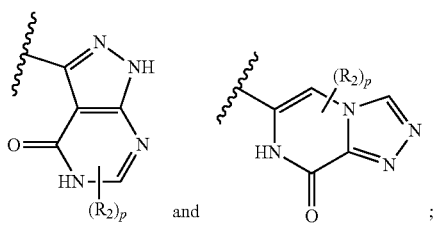

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having one or two oxygen heteroatoms and optionally, is substituted with =O, selected from:

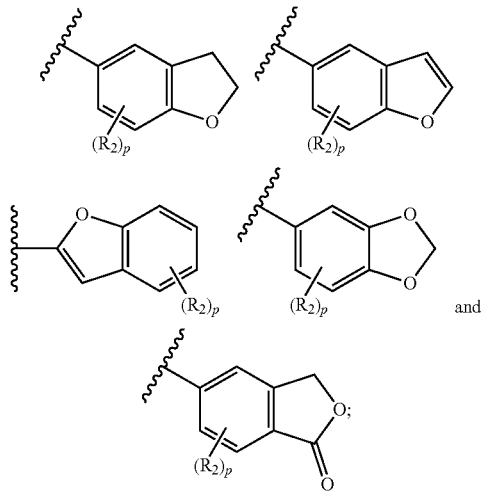

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having one or two nitrogen heteroatoms and one oxygen heteroatom and optionally, is substituted with =O, selected from:

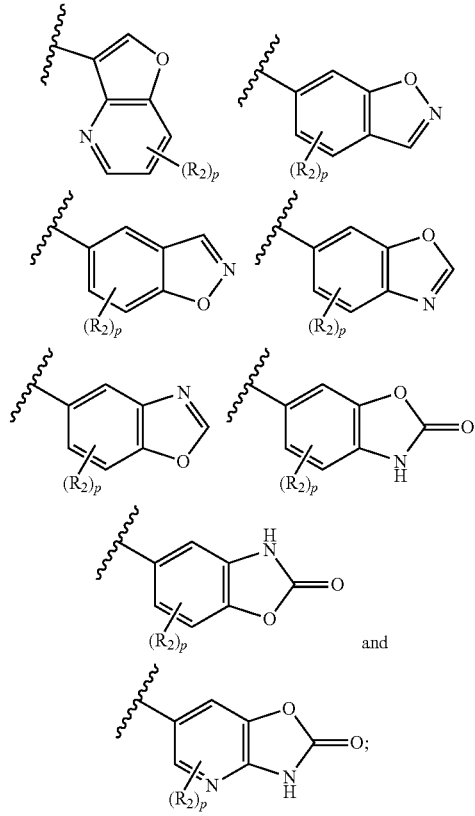

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having one or two nitrogen heteroatoms and one sulfur heteroatom, selected from:

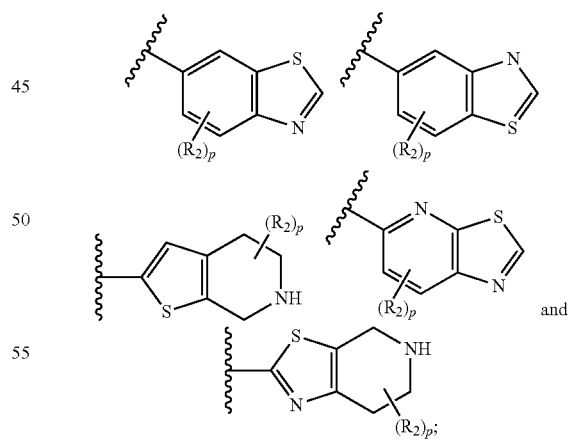

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 9-membered heterocyclic ring having two nitrogen heteroatoms and one oxygen heteroatom, and is substituted with =O, selected from:

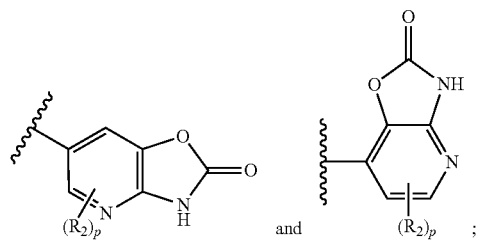

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 10-membered heterocyclic ring having one nitrogen heteroatom, selected from:

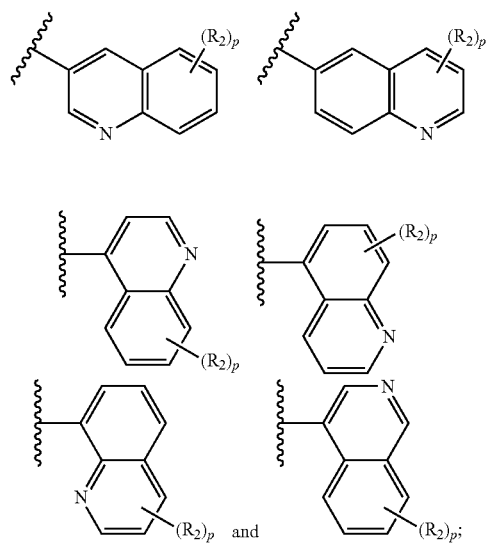

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 10-membered heterocyclic ring having two nitrogen heteroatoms, selected from:

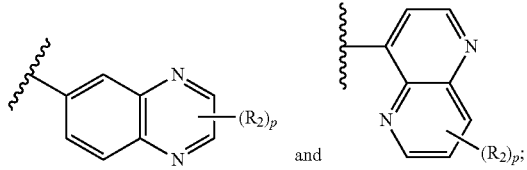

and L, $R_{1a}$, $R_{1b}$, $R_2$, $R_4$, $R_5$, m, n, p, x, and y are defined in the first aspect.

One embodiment provides a compound of Formula (I) or a salt thereof, wherein each of $G_1$ and $G_2$ is independently a 10-membered heterocyclic ring having one or two nitrogen heteroatoms and one oxygen heteroatom, and is optionally substituted with =O, selected from:

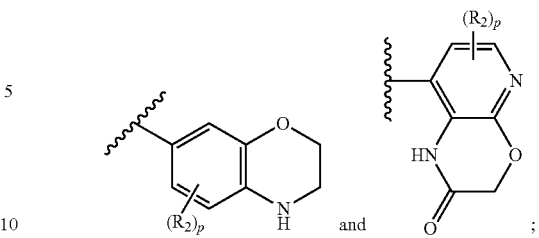

and L, $R_{1a}$, $R_{1b}$, $R_2$, $R_4$, $R_5$, m, n, p, x, and y are defined in the first aspect.

One embodiment provides a compound of Formula (I), N-oxide, or a salt thereof wherein each of $G_1$ and $G_2$ is independently:

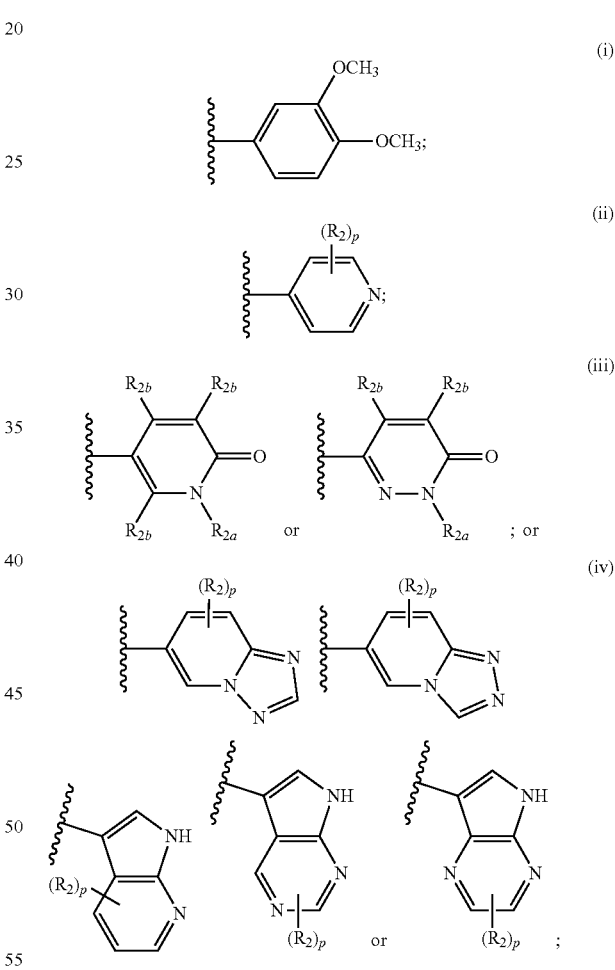

and L $R_{1a}$, $R_{1b}$, $R_{2a}$, $R_{2b}$, $R_2$, $R_4$, $R_5$, m, n, p, x, and y are defined in the first aspect. Included in this embodiment are compounds in which $R_{1a}$ and $R_{1b}$ are independently —$CH_2CH_3$ or —$CH(CH_3)_2$; each $R_2$ is independently —$CH_3$ or —$OCH_3$; each $R_{2a}$ is —$CH_3$; each $R_{2b}$ is independently H, Cl, or —$CH_3$; each $R_4$ is independently F, —$CH_3$, or —$OCH_3$; and each $R_5$ is independently F, Cl, —CN, —$CH_3$, —$CF_3$, or —$OCH_3$.

One embodiment provides a compound of Formula (I) or a salt thereof wherein $G_1$ and $G_2$ are each

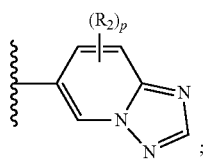

and L, $R_{1a}$, $R_{1b}$, $R_2$, $R_4$, $R_5$, m, n, p, x, and y are defined in the first aspect. Included in this embodiment are compounds in which each $R_2$ is independently —CH$_3$ or —OCH$_3$. Also included in this embodiment are compounds in which each $R_2$ is —OCH$_3$.

One embodiment provides a compound of Formula (I) or a salt thereof wherein $G_1$ and $G_2$ are each

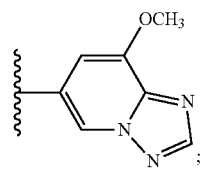

and L, $R_{1a}$, $R_{1b}$, $R_4$, $R_5$, m, n, x, and y are defined in the first aspect. Included in this embodiment are compounds in which $R_{1a}$ and $R_{1b}$ are independently H, Cl, —CN, $C_{1-4}$ alkyl, or $C_{1-2}$ fluoroalkyl. Also included in this embodiment are compounds in which $R_{1a}$ and $R_{1b}$ are independently —CH$_2$CH$_3$ or —CH(CH$_3$)$_2$.

One embodiment provides a compound of Formula (I), N-oxide, or a salt thereof wherein: L is —(CH$_2$)$_q$— or -L$_1$-NR$_x$C(O)—(CH$_2$)$_t$—C(O)NR$_x$-L$_2$-; q is an integer in the range of 8 to 26; t is an integer in the range of 2 to 16; and $G_1$, $G_2$, $L_1$, $L_2$, $R_{1a}$, $R_{1b}$, $R_{1b}$, $R_{2a}$, $R_{2b}$, $R_{2c}$, $R_{2a}$, $R_4$, $R_5$, $R_x$, m, n, x, p, and y are defined in the first aspect. Included in this embodiment are compounds in which q is an integer in the range of from 10 to 24; and t is an integer in the range of 2 to 16. Also included in this embodiment are compounds in which q is an integer in the range of from 16 to 20; and t is an integer in the range of 2 to 12. Additionally, included in this embodiment are compounds in which q is 16, 17, or 18; and t is an integer in the range of 2 to 12.

One embodiment provides a compound of Formula (I), N-oxide, or a salt thereof wherein: L is —(CH$_2$)$_q$—; q is an integer in the range of 8 to 26; and $G_1$, $G_2$, $R_{1a}$, $R_{1b}$, $R_{1b}$, $R_{2a}$, $R_{2b}$, $R_{2c}$, $R_{2a}$, $R_4$, $R_5$, m, n, x, and y are defined in the first aspect. Included in this embodiment are compounds in which q is an integer in the range of 10 to 24. Also included are compounds in which q is an integer in the range of 16 to 20. Additionally, included in this embodiment are compounds in which q is 16, 17, or 18.

One embodiment provides a compound of Formula (I), N-oxide, or a salt thereof wherein: L is -L$_1$-NR$_x$C(O)—(CH$_2$)$_t$—C(O)NR$_x$-L$_2$-; t is an integer in the range of 2 to 16; and $G_1$, $G_2$, $L_1$, $L_2$, $R_{1a}$, $R_{1b}$, $R_{2a}$, $R_{2b}$, $R_{2c}$, $R_{2a}$, $R_4$, $R_5$, $R_x$, m, n, p, x, and y are defined in the first aspect. Included in this embodiment are compounds in which t is an integer in the range of 2 to 16. Also included in this embodiment are compounds in which t is an integer in the range of 2 to 12. Additionally, included in this embodiment are compounds in which t is an integer in the range of 2 to 12; and $L_1$ and $L_2$ are each —(CH$_2$)$_2$—.

One embodiment provides a compound of Formula (I), N-oxide, or a salt thereof wherein: $R_{1a}$ and $R_{1b}$ are independently H, Cl, —CN, $C_{1-4}$ alkyl, $C_{1-3}$ fluoroalkyl, $C_{1-3}$ hydroxy-fluoroalkyl, $C_{3-6}$ cycloalkyl, —CH$_2$(C$_{3-6}$ cycloalkyl), —C(O)O(C$_{1-3}$ alkyl), or tetrahydropyranyl; each $R_2$ is independently halo, —CN, —OH, —NO$_2$, $C_{1-3}$ alkyl, $C_{1-2}$ fluoroalkyl, $C_{1-3}$ hydroxyalkyl, $C_{1-3}$ aminoalkyl, —(CH$_2$)$_{0-4}$ O(C$_{1-3}$ alkyl), $C_{1-3}$ fluoroalkoxy, $C_{2-4}$ alkoxyalkoxy, —O(CH$_2$)$_{1-2}$NR$_x$R$_x$, —C(O)O(C$_{1-3}$ alkyl), —C(O)NR$_y$R$_y$, —NR$_y$R$_y$, —NR$_x$C(O)(C$_{1-3}$ alkyl), —NR$_x$(CH$_2$-cyclopropyl), $C_{3-6}$ cycloalkyl, methylpiperidinyl, methylpiperazinyl, amino-oxadiazolyl, imidazolyl, triazolyl, or —C(O)(thiazolyl); each $R_4$ is independently F, —OH, $C_{1-2}$ alkyl, or —OCH$_3$; or two $R_4$ attached to the same carbon atom form =O; each $R_5$ is independently F, Cl, —CN, $C_{1-2}$ alkyl, $C_{1-2}$ fluoroalkyl, or —OCH$_3$; and $G_1$, $G_2$, L, $R_{2a}$, $R_{2b}$, $R_{2c}$, $R_{2a}$, $R_x$, $R_y$, m, n, p, x, and y are defined in the first aspect. Included in this embodiment are compounds in which m is zero, 1, or 2; n is zero, 1, or 2; p is zero, 1, or 2; x is zero, or 1; and y is zero, or 1.

One embodiment provides a compound of Formula (I), N-oxide, or a salt thereof wherein: $R_{1a}$ and $R_{1b}$ are independently H, Cl, —CN, $C_{1-4}$ alkyl, or $C_{1-2}$ fluoroalkyl; each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-3}$ aminoalkyl, —O(CH$_2$)$_{1-2}$OH, —O(C$_{1-4}$ alkyl), $C_{1-2}$ fluoroalkoxy, —(CH$_2$)$_{1-4}$O(C$_{1-3}$ alkyl), —O(CH$_2$)$_{1-2}$OC(O)(C$_{1-3}$ alkyl), —O(CH$_2$)$_{1-2}$NR$_x$R$_x$, —C(O)O(C$_{1-3}$ alkyl), —C(O)NR$_y$R$_y$, —NR$_y$R$_y$, —NR$_y$(C$_{1-3}$ fluoroalkyl), —NR$_y$(C$_{1-4}$ hydroxyalkyl), —NR$_x$CH$_2$(phenyl), —NR$_x$S(O)$_2$(C$_{3-6}$ cycloalkyl), —NR$_x$C(O)(C$_{1-3}$ alkyl), —NR$_x$(CH$_2$-cyclopropyl), $C_{3-6}$ cycloalkyl, morpholinyl, dioxothiomorpholinyl, methylpiperidinyl, methylpiperazinyl, amino-oxadiazolyl, imidazolyl, triazolyl, or —C(O)(thiazolyl); $R_5$ is F, Cl, —CN, $C_{1-2}$ alkyl, or —OCH$_3$; m is zero; n is zero; and $G_1$, $G_2$, L, $R_{2b}$, $R_{2c}$, $R_{2a}$, $R_4$, $R_x$, $R_y$, x, and y are defined in the first aspect.

One embodiment provides a compound of Formula (I), N-oxide, or a salt thereof wherein m is zero, 1, or 2; n is zero, 1, or 2; and $G_1$, $G_2$, L, $R_{1b}$, $R_{2a}$, $R_{2b}$, $R_{2c}$, $R_{2a}$, $R_4$, $R_5$, $R_x$, $R_y$, x, and y are defined in the first aspect.

One embodiment provides a compound of Formula (I), N-oxide, or a salt thereof wherein: $G_1$ and $G_2$ are each

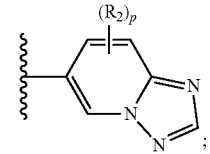

$R_{1a}$ and $R_{1b}$ are each —CH(CH$_3$)$_2$; each $R_2$ is —OCH$_3$; L is —(CH$_2$)$_{18}$— or -L$_1$-NR$_x$C(O)—(CH$_2$)$_t$—C(O)NR$_x$-L$_2$-; $L_1$ and $L_2$ are each —(CH$_2$)$_2$—; t is an integer in the range of 2 to 12; m is zero; n is zero; each p is 1; x is zero; and y is zero. Included in this embodiment are compounds in which $G_1$ and $G_2$ are each

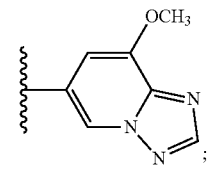 [SMILES: *c1cc(OC)c2ncnn2c1]

One embodiment provides a compound of Formula (I) or a salt thereof, wherein said compound is:

N1,N13-bis(2-(4-(3-isopropyl-2-(8-methoxy-[1,2,4]tri-azolo[1,5-a]pyridin-6-yl)-1H-indol-5-yl)piperidin-1-yl)ethyl)tridecanediamide (1);

N1,N14-bis(2-(4-(3-isopropyl-2-(8-methoxy-[1,2,4]tri-azolo[1,5-a]pyridin-6-yl)-1H-indol-5-yl)piperidin-1-yl)ethyl)tetradecanediamide (2);

N1,N12-bis(2-(4-(3-isopropyl-2-(8-methoxy-[1,2,4]tri-azolo[1,5-a]pyridin-6-yl)-1H-indol-5-yl)piperidin-1-yl)ethyl)dodecanediamide (3);

N1,N11-bis(2-(4-(3-isopropyl-2-(8-methoxy-[1,2,4]tri-azolo[1,5-a]pyridin-6-yl)-1H-indol-5-yl)piperidin-1-yl)ethyl)undecanediamide (4);

N1,N9-bis(2-(4-(3-isopropyl-2-(8-methoxy-[1,2,4]tri-azolo[1,5-a]pyridin-6-yl)-1H-indol-5-yl)piperidin-1-yl)ethyl)nonanediamide (5);

N1,N8-bis(2-(4-(3-isopropyl-2-(8-methoxy-[1,2,4]tri-azolo[1,5-a]pyridin-6-yl)-1H-indol-5-yl)piperidin-1-yl)ethyl)octanediamide (6);

N1,N10-bis(2-(4-(3-isopropyl-2-(8-methoxy-[1,2,4]tri-azolo[1,5-a]pyridin-6-yl)-1H-indol-5-yl)piperidin-1-yl)ethyl)decanediamide (7);

N1,N7-bis(2-(4-(3-isopropyl-2-(8-methoxy-[1,2,4]tri-azolo[1,5-a]pyridin-6-yl)-1H-indol-5-yl)piperidin-1-yl)ethyl)heptanediamide (8);

N1,N6-bis(2-(4-(3-isopropyl-2-(8-methoxy-[1,2,4]tri-azolo[1,5-a]pyridin-6-yl)-1H-indol-5-yl)piperidin-1-yl)ethyl)adipamide (9);

N1,N12-bis(2-(4-(3-isopropyl-2-(8-methoxy-[1,2,4]tri-azolo[1,5-a]pyridin-6-yl)-1H-indol-5-yl)piperidin-1-yl)ethyl)dodecanediamide (10);

N1,N4-bis(2-(4-(3-isopropyl-2-(8-methoxy-[1,2,4]tri-azolo[1,5-a]pyridin-6-yl)-1H-indol-5-yl)piperidin-1-yl)ethyl)succinamide (11); or 1,18-bis(4-(3-isopropyl-2-(8-methoxy-[1,2,4]triazolo[1,5-a]pyridin-6-yl)-1H-indol-5-yl) piperidin-1-yl)octadecane (12).

The present invention may be embodied in other specific forms without departing from the spirit or essential attributes thereof. The invention encompasses all combinations of the aspects and/or embodiments of the invention noted herein. It is understood that any and all embodiments of the present invention may be taken in conjunction with any other embodiment or embodiments to describe additional embodiments. It is also to be understood that each individual element of the embodiments is meant to be combined with any and all other elements from any embodiment to describe an additional embodiment.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phrase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group —NH$_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include Cl, $C_2$, $C_3$, and $C_4$ alkyl groups substituted with one or more fluorine atoms. Representative examples of fluoroalkyl groups include, but are not limited to, —CF$_3$ and —CH$_2$CF$_3$.

The term "cyanoalkyl" includes both branched and straight-chain saturated alkyl groups substituted with one or more cyano groups. For example, "cyanoalkyl" includes —CH$_2$CN, —CH$_2$CH$_2$CN, and $C_{1-4}$ cyanoalkyl.

The term "aminoalkyl" includes both branched and straight-chain saturated alkyl groups substituted with one or more amine groups. For example, "aminoalkyl" includes —CH$_2$NH$_2$, —CH$_2$CH$_2$NH$_2$, and $C_{1-4}$ aminoalkyl.

The term "hydroxyalkyl" includes both branched and straight-chain saturated alkyl groups substituted with one or more hydroxyl groups. For example, "hydroxyalkyl" includes —CH$_2$OH, —CH$_2$CH$_2$OH, and C$_{1-4}$ hydroxyalkyl.

The term "hydroxy-fluoroalkyl" includes both branched and straight-chain saturated alkyl groups substituted with one or more hydroxyl groups and one or more fluorine atoms. For example, "hydroxy-fluoroalkyl" includes —CHFCH$_2$OH, —CH$_2$CHFC(CH$_3$)$_2$OH, and C$_{1-4}$ hydroxyfluoroalkyl.

The term "cycloalkyl" as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "C$_3$-C$_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—OCH$_3$). For example, "C$_{1-3}$ alkoxy" denotes alkoxy groups with one to three carbon atoms.

The term "alkoxyalkyl," as used herein, refers to an alkoxy group attached through its oxygen atom to an alkyl group, which is attached to the parent molecular moiety, for example, methoxymethyl group (—CH$_2$OCH$_3$). For example, "C$_{2-4}$ alkoxyalkyl" denotes alkoxyalkyl groups with two to four carbon atoms, such as —CH$_2$OCH$_3$, —CH$_2$CH$_2$OCH$_3$, —CH$_2$OCH$_2$CH$_3$, and —CH$_2$CH$_2$OCH$_2$CH$_3$.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in:
a) *The Practice of Medicinal Chemistry*, Camille G. Wermuth et al., Ch 31, (Academic Press, 1996);
b) *Design of Prodrugs*, edited by H. Bundgaard, (Elsevier, 1985);
c) *A Textbook of Drug Design and Development*, P. Krogsgaard-Larson and H. Bundgaard, eds. Ch 5, pgs 113-191 (Harwood Academic Publishers, 1991); and
d) *Hydrolysis in Drug and Prodrug Metabolism*, Bernard Testa and Joachim M. Mayer, (Wiley-VCH, 2003).

Preparation of prodrugs is well known in the art and described in, for example, King, F. D., ed., *Medicinal Chemistry: Principles and Practice*, The Royal Society of Chemistry, Cambridge, UK (1994); Testa, B. et al., *Hydrolysis in Drug and Prodrug Metabolism. Chemistry, Biochemistry and Enzymology*, VCHA and Wiley-VCH, Zurich, Switzerland (2003); Wermuth, C. G., ed., *The Practice of Medicinal Chemistry*, Academic Press, San Diego, CA (1999); Rautio, J. et al., *Nature Review Drug Discovery*, 17, 559-587, (2018).

In addition, compounds of Formula (I), subsequent to their preparation, can be isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor to TLR7/8/9, or effective to treat or prevent autoimmune and/or inflammatory disease states, such as SLE, IBD, multiple sclerosis (MS), and Sjögren's syndrome, and rheumatoid arthritis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl (—CH$_3$) also includes deuterated methyl groups such as —CD$_3$.

Utility

The human immune system has evolved to defend the body from micro-organisms, viruses, and parasites that can cause infection, disease or death. Complex regulatory mechanisms ensure that the various cellular components of the immune system target the foreign substances or organisms, while not causing permanent or significant damage to the individual. While the initiating events are not well understood at this time, in autoimmune disease states the immune system directs its inflammatory response to target organs in the afflicted individual. Different autoimmune diseases are typically characterized by the predominate or initial target organ or tissues affected; such as the joint in the case of rheumatoid arthritis, the thyroid gland in the case of Hashimoto's thyroiditis, the central nervous system in the case of multiple sclerosis, the pancreas in the case of type I diabetes, and the bowel in the case of inflammatory bowel disease.

The compounds of the invention inhibit signaling through Toll-like receptor 7, or 8, or 9 (TLR7, TLR8, TLR9) or combinations thereof. Accordingly, compounds of Formula (I) have utility in treating conditions associated with the inhibition of signaling through one or more of TLR7, TLR8, or TLR9. Such conditions include TLR7, TLR8, or TLR9 receptor associated diseases in which cytokine levels are modulated as a consequence of intracellular signaling.

As used herein, the terms "treating" or "treatment" encompass the treatment of a disease state in a mammal, particularly in a human, and include: (a) preventing or delaying the occurrence of the disease state in a mammal, in particular, when such mammal is predisposed to the disease state but has not yet been diagnosed as having it; (b) inhibiting the disease state, i.e., arresting its development; and/or (c) achieving a full or partial reduction of the symptoms or disease state, and/or alleviating, ameliorating, lessening, or curing the disease or disorder and/or its symptoms.

In view of their activity as selective inhibitors of TLR7, TLR8, or TLR9, compounds of Formula (I) are useful in treating TLR7, TLR8, or TLR9 family receptor associated diseases, but not limited to, inflammatory diseases such as Crohn's disease, ulcerative colitis, asthma, graft versus host disease, allograft rejection, chronic obstructive pulmonary disease; autoimmune diseases such as Graves' disease, rheumatoid arthritis, systemic lupus erythematosus, lupus nephritis, cutaneous lupus, psoriasis; auto-inflammatory diseases including Cryopyrin-Associated Periodic Syndromes (CAPS), TNF Receptor Associated Periodic Syndrome (TRAPS), Familial Mediterranean Fever (FMF), adult onset stills, systemic onset juvenile idiopathic arthritis, gout, gouty arthritis; metabolic diseases including type 2 diabetes, atherosclerosis, myocardial infarction; destructive bone disorders such as bone resorption disease, osteoarthritis, osteoporosis, multiple myeloma-related bone disorder; proliferative disorders such as acute myelogenous leukemia, chronic myelogenous leukemia; angiogenic disorders such as angiogenic disorders including solid tumors, ocular neovascularization, and infantile haemangiomas; infectious diseases such as sepsis, septic shock, and Shigellosis; neurodegenerative diseases such as Alzheimer's disease, Parkinson's disease, cerebral ischemias or neurodegenerative disease caused by traumatic injury, oncologic and viral diseases such as metastatic melanoma, Kaposi's sarcoma, multiple myeloma, and HIV infection and CMV retinitis, AIDS, respectively.

More particularly, the specific conditions or diseases that may be treated with the inventive compounds include, without limitation, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, keloid formation, scar tissue formation, ulcerative colitis, pyresis, influenza, osteoporosis, osteoarthritis, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hypoxia, vascular hyperplasia, cardiac and renal reperfusion injury, thrombosis, cardiac hypertrophy, thrombin-induced platelet aggregation, endotoxemia and/or toxic shock syndrome, conditions associated with prostaglandin endoperoxidase syndase-2, and pemphigus vulgaris. Included in this embodiment are methods of treatment in which the condition is selected from lupus including lupus nephritis and systemic lupus erythematosus (SLE), Crohn's disease, ulcerative colitis, allograft rejection, rheumatoid arthritis, psoriasis, ankylosing spondylitis, psoriatic arthritis, and pemphigus vulgaris. Also included are methods of treatment in which the condition is selected from ischemia reperfusion injury, including cerebral ischemia reperfusions injury arising from stroke and cardiac ischemia reperfusion injury arising from myocardial infarction. Another method of treatment is one in which the condition is multiple myeloma.

In one embodiment, the compounds of Formula (I) are useful in treating cancer, including Waldenstrom's Macroglobulinemia (WM), diffuse large B cell lymphoma (DLBCL), chronic lymphocytic leukemia (CLL), cutaneous diffuse large B cell lymphoma, and primary CNS lymphoma.

In addition, the TLR7, TLR8, or TLR9 inhibitors of the present invention inhibit the expression of inducible pro-inflammatory proteins such as prostaglandin endoperoxide synthase-2 (PGHS-2), also referred to as cyclooxygenase-2 (COX-2), IL-1, IL-6, IL-18, chemokines. Accordingly, additional TLR7/8/9 associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retrovirus infections, including feline immunodeficiency virus, bovine immunodeficiency virus, and canine immunodeficiency virus.

The present invention thus provides methods for treating such conditions, comprising administering to a subject in need thereof a therapeutically-effective amount of at least one compound of Formula (I) or a salt thereof. "Therapeutically effective amount" is intended to include an amount of a compound of the present invention that is effective when administered alone or in combination to inhibit autoimmune disease or chronic inflammatory disease.

The methods of treating TLR7, TLR8, or TLR9 associated conditions may comprise administering compounds of Formula (I) alone or in combination with each other and/or other suitable therapeutic agents useful in treating such conditions. Accordingly, "therapeutically effective amount" is also intended to include an amount of the combination of compounds claimed that is effective to inhibit TLR7, TLR8, or TLR9 and/or treat diseases associated with TLR7, TLR8, or TLR9.

Exemplary of such other therapeutic agents include corticosteroids, rolipram, calphostin, cytokine-suppressive anti-inflammatory drugs (CSAIDs), Interleukin-10, glucocorticoids, salicylates, nitric oxide, and other immunosuppressants; nuclear translocation inhibitors, such as deoxyspergualin (DSG); non-steroidal anti-inflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); anti-malarials such as hydroxychloroquine; cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the *Physicians'Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR7/8/9 receptor-associated conditions, including IL-1 family receptor-mediated diseases as described above.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A "pharmaceutically acceptable carrier" refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington's Pharmaceutical Sciences,* 17th Edition (1985), which is incorporated herein by reference in its entirety.

Compounds in accordance with Formula (I) can be administered by any means suitable for the condition to be treated, which can depend on the need for site-specific treatment or quantity of Formula (I) compound to be delivered.

Also embraced within this invention is a class of pharmaceutical compositions comprising a compound of Formula (I) and one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parenterally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride solution, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and (c) a package insert stating that the pharmaceutical composition can be used for the treatment of an inflammatory disorder and/or an autoimmune disease (as defined previously). In another embodiment, the package insert states that the pharmaceutical composition can be used in combination (as defined previously) with a second therapeutic agent to treat an inflammatory disorder and/or an autoimmune disease. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). In one embodiment, the package insert specifically recites the indications for which the pharmaceutical composition has been approved. The package insert may be made of any material on which a person can read information contained therein or thereon. For example, the package insert is a printable material (e.g., paper, plastic, cardboard, foil, adhesive-backed paper or plastic, etc.) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety by reference.

The compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene and Wuts (*Protective Groups In Organic Synthesis*, Third Edition, Wiley and Sons, 1999).

EXAMPLES

Preparation of compounds of Formula (I), and intermediates used in the preparation of compounds of Formula (I), can be prepared using procedures shown in the following Examples and related procedures. The methods and conditions used in these examples, and the actual compounds prepared in these Examples, are not meant to be limiting, but are meant to demonstrate how the compounds of Formula (I) can be prepared. Starting materials and reagents used in these examples, when not prepared by a procedure described herein, are generally either commercially available, or are reported in the chemical literature, or may be prepared by using procedures described in the chemical literature.

ABBREVIATIONS

Ac acetyl
ACN acetonitrile
AcOH acetic acid
anhyd. anhydrous
aq. aqueous
Bn benzyl
Bu butyl
Boc tert-butoxycarbonyl
CV Column Volumes
DCE dichloroethane
DCM dichloromethane
DMAP dimethylaminopyridine
DMF dimethylformamide
DMSO dimethylsulfoxide
EDC 1-(3-dimethylaminopropyl)-3-ethylcarbodiimide hydrochloride
EtOAc ethyl acetate
Et ethyl
EtOH ethanol
H or $H_2$ hydrogen
h, hr or hrs hour(s)
HCTU O-(6-Chlorobenzotriazol-1-yl)-N,N,N',N'-tetramethyluronium hexafluorophosphate
hex hexane
i iso
IPA isopropyl alcohol
HOAc acetic acid
HCl hydrochloric acid
HPLC high pressure liquid chromatography
LC liquid chromatography
M molar
mM millimolar
Me methyl
MeOH methanol
MHz megahertz
min. minute(s)
mins minute(s)
$M^{+1}$ $(M+H)^+$
MS mass spectrometry
n or N normal
NBS n-bromosuccinimide
nm nanometer
nM nanomolar
NMP N-methylpyrrolidine
Pd/C palladium on carbon
$PdCl_2(dppf)_2$ [1,1'-bis(diphenylphosphino)ferrocene]dichloropalladium(II)
$Pd(PPh_3)_4$ tetrakis(triphenylphosphine)palladium
Ph phenyl
$PPh_3$ triphenylphosphine
Pr propyl
PSI pounds per square inch
PyBOP bromotripyrrolidinophosphonium hexafluorophosphate
Ret Time retention time
sat. saturated
SFC supercritical fluid chromatography
TEA triethylamine
TFA trifluoroacetic acid THF tetrahydrofuran
Analytical and Preparative HPLC Conditions:
QC-ACN-AA-XB: Column: Waters Acquity UPLC BEH C18, 2.1×50 mm, 1.7 µm particles; Mobile Phase A: 5:95 acetonitrile:water with 10 mM ammonium acetate; Mobile Phase B: 95:5 acetonitrile:water with 10 mM ammonium acetate; Temperature: 50° C.; Gradient: 0-100% B over 3 minutes, then a 0.75-minute hold at 100% B; Flow: 1.0 mL/min; Detection: UV at 220 nm.
QC-ACN-TFA-XB: Column: Waters Acquity UPLC BEH C18, 2.1×50 mm, 1.7 µm particles; Mobile Phase A: 5:95 acetonitrile:water with 0.1% trifluoroacetic acid; Mobile Phase B: 95:5 acetonitrile:water with 0.1% trifluoroacetic acid; Temperature: 50° C.; Gradient: 0-100% B over 3 minutes, then a 0.75-minute hold at 100% B; Flow: 1.0 mL/min; Detection: UV at 220 nm.
(TS): Column: Waters Acquity UPLC BEH C18 (2.1×50 mm), 1.7 micron; Solvent A=100% water with 0.05% TFA; Solvent B=100% acetonitrile with 0.05% TFA; gradient=2-98% B over 1 minute, then a 0.5-minute hold at 98% B; Flow rate: 0.8 mL/min; Detection: UV at 254 nm.

Example 1

N1,N13-bis(2-(4-(3-isopropyl-2-(8-methoxy-[1,2,4]triazolo[1,5-a]pyridin-6-yl)-1H-indol-5-yl)piperidin-1-yl)ethyl)tridecanediamide

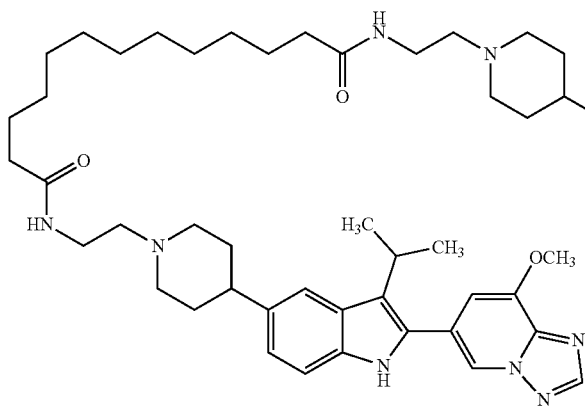

(1)

Intermediate 1A: 2-(4-(3-isopropyl-2-(8-methoxy-[1,2,4]triazolo[1,5-a]pyridin-6-yl)-1H-indol-5-yl)piperidin-1-yl)ethan-1-amine

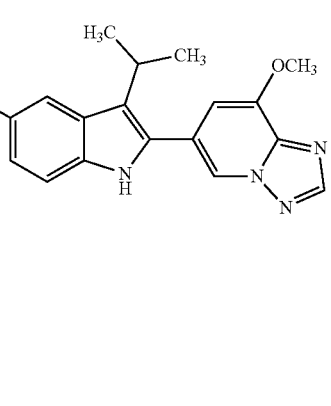

(1A)

To a 20 ml scintillation vial was added tert-butyl 4-(3-isopropyl-2-(8-methoxy-[1,2,4]triazolo[1,5-a]pyridin-6-yl)-1H-indol-5-yl)piperidine-1-carboxylate (200 mg, 0.408 mmol), DCM (3 mL), and TFA (3 mL). The reaction was stirred at room temperature for 30 minutes at which time LCMS indicated that the Boc deprotection was complete. The vial was concentrated under a stream of $N_2$ and triturated with ether several times at which point a solid forms. Product was dissolved in DMF (5 mL) and DIEA (0.214 mL, 1.225 mmol) was added followed by addition of tert-butyl (2-oxoethyl)carbamate (195 mg, 1.225 mmol). After 30 minutes, sodium triacetoxyborohydride (260 mg, 1.225 mmol) was added. The reaction mixture was stirred for 2 hours. The reaction mixture was diluted with ethyl acetate and washed with saturated NaCl. The organic layer was dried with $MgSO_4$, filtered and concentrated. Crude product was purified on silica gel (DCM/MeOH 0-15%) to afford tert-butyl (2-(4-(3-isopropyl-2-(8-methoxy-[1,2,4]triazolo[1,5-a]pyridin-6-yl)-1H-indol-5-yl)piperidin-1-yl)ethyl)carbamate which was immediately treated with TFA/DCM for 30 minutes. LCMS show removal of Boc group. The solvents were removed in vacuo. Material was diluted with ethyl acetate and washed with sat $NaHCO_3$. The organic layer was dried with $MgSO_4$, filtered and concentrated to afford 2-(4-(3-isopropyl-2-(8-methoxy-[1,2,4]triazolo[1,5-a]pyridin-6-yl)-1H-indol-5-yl) piperidin-1-yl)ethan-1-amine (72 mg, 0.166 mmol, 40.7% yield). LCMS retention time 0.6 min [TS]. MS ($E^+$) m/z: 433.3 (M+H).

Example 1

To a mixture of tridecanedioic acid (6.78 mg, 0.028 mmol) and DIEA (0.015 mL, 0.083 mmol) in DMF (2 mL) was added HATU (21.10 mg, 0.055 mmol). After 30 minutes, 2-(4-(3-isopropyl-2-(8-methoxy-[1,2,4]triazolo[1,5-a]pyridin-6-yl)-1H-indol-5-yl)piperidin-1-yl)ethan-1-amine (24 mg, 0.055 mmol) was added. The reaction mixture was stirred for one hour. The reaction mixture was filtered and purified by HPLC to afford N1,N13-bis(2-(4-(3-isopropyl-2-(8-methoxy-[1,2,4]triazolo[1,5-a]pyridin-6-yl)-1H-indol-5-yl)piperidin-1-yl)ethyl)tridecanediamide (12.4 mg, 0.011 mmol, 40.8% yield). LCMS retention time 0.77 min [TS]. MS ($E^+$) m/z: 1073.8 (M+H). $^1$H NMR (500 MHz, DMSO-$d_6$) δ 11.25 (s, 2H), 8.61-8.55 (m, 2H), 8.53-8.49 (m, 2H), 8.22-8.12 (m, 2H), 7.62-7.55 (m, 2H), 7.37 (d, J=8.2 Hz, 2H), 7.16 (s, 2H), 7.04 (br d, J=8.5 Hz, 2H), 4.11-4.04 (m, 6H), 3.66 (br d, J=11.0 Hz, 2H), 3.23-3.09 (m, 6H), 2.98-2.78 (m, 2H), 2.54-2.48 (m, 9H), 2.21-1.90 (m, 12H), 1.57-1.48 (m, 4H), 1.48-1.42 (m, 12H), 1.34-1.17 (m, 15H).

The following examples were prepared according to the general procedures described in the above examples.

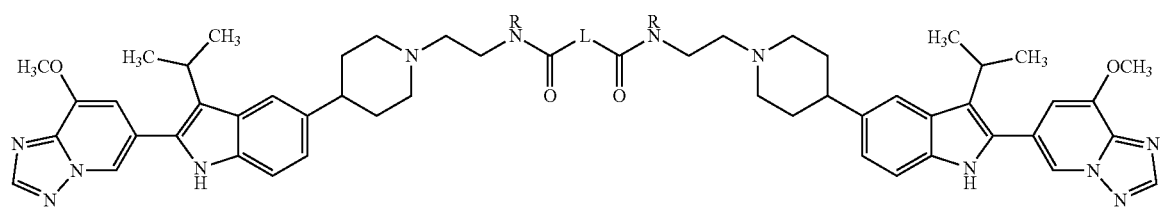

TABLE 1

| Ex. No. | -NRC(O)-L-C(O)NR- | Mol. Wt. | LCMS M+ | Ret Time (min) | HPLC Method |
|---|---|---|---|---|---|
| 2 | —NHC(O)—(CH$_2$)$_{12}$—C(O)NH— | 1087.5 | 1087.8 | 1.79 | QC-ACN-AA-XB |
| 3 | —NHC(O)—(CH$_2$)$_{10}$—C(O)NH— | 1059.4 | 1060.0 | 1.89 | QC-ACN-AA-XB |
| 4 | —NHC(O)—(CH$_2$)$_9$—C(O)NH— | 1045.4 | 1045.8 | 1.76 | QC-ACN-AA-XB |
| 5 | —NHC(O)—(CH$_2$)$_7$—C(O)NH— | 1017.3 | 1017.5 | 1.65 | QC-ACN-AA-XB |
| 6 | —NHC(O)—(CH$_2$)$_6$—C(O)NH— | 1003.3 | 1003.8 | 1.38 | QC-ACN-AA-XB |
| 7 | —NHC(O)—(CH$_2$)$_8$—C(O)NH— | 1031.4 | 1031.4 | 1.66 | QC-ACN-AA-XB |
| 8 | —NHC(O)—(CH$_2$)$_5$—C(O)NH— | 989.3 | 989.8 | 1.49 | QC-ACN-AA-XB |
| 9 | —NHC(O)—(CH$_2$)$_4$—C(O)NH— | 975.2 | 976.1 | 1.49 | QC-ACN-AA-XB |
| 10 | —N(CH$_3$)C(O)—(CH$_2$)$_{10}$—C(O)N(CH$_3$)— | 1087.5 | 1087.6 | 2.32 | QC-ACN-AA-XB |
| 11 | —NHC(O)—(CH$_2$)$_2$—C(O)NH— | 947.2 | 948.4 | 1.59 | QC-ACN-AA-XB |

Example 12

1,18-bis(4-(3-isopropyl-2-(8-methoxy-[1,2,4]triazolo[1,5-a]pyridin-6-yl)-1H-indol-5-yl) piperidin-1-yl)octadecane

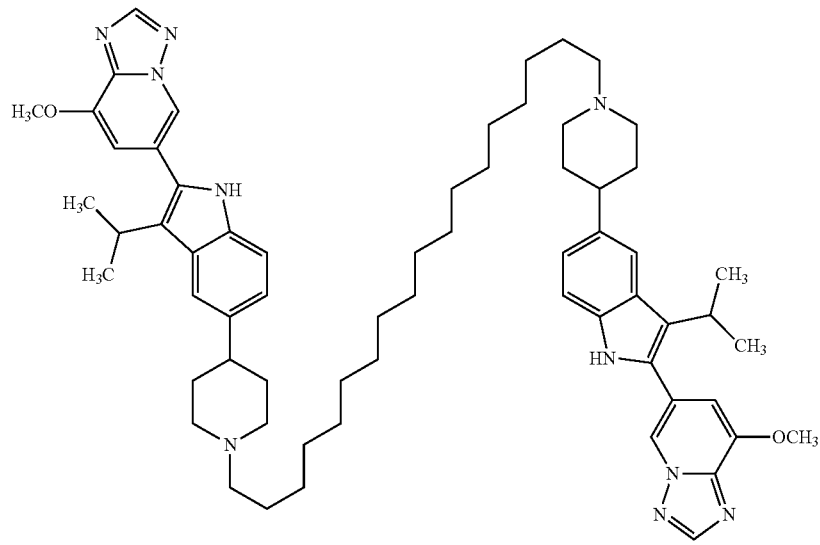

(12)

To a mixture of 6-(3-isopropyl-5-(piperidin-4-yl)-1H-indol-2-yl)-8-methoxy-[1,2,4]triazolo[1,5-a]pyridine (21.73 mg, 0.056 mmol) and potassium carbonate (15.42 mg, 0.112 mmol) in DMF (2 mL) was added 1,18-dibromooctadecane (11.5 mg, 0.028 mmol). The reaction mixture was stirred at room temperature for 1 hour, heated to 70° C., and stirred overnight. The reaction mixture was cooled, filtered, and purified by HPLC to afford 1,18-bis(4-(3-isopropyl-2-(8-methoxy-[1,2,4]triazolo[1,5-a]pyridin-6-yl)-1H-indol-5-yl)piperidin-1-yl)octadecane (8 mg, 7.62 μmol, 27.3% yield). LCMS retention time 2.65 min [QC-ACN-AA-XB]. MS (E$^+$) m/z: 1030.07 (M+H). $^1$H NMR (500 MHz, DMSO-d$_6$) δ 11.24 (s, 2H), 8.53 (s, 2H), 8.50 (s, 2H), 7.58 (s, 2H), 7.37 (d, J=8.5 Hz, 2H), 7.13 (s, 2H), 7.04 (br d, J=8.2 Hz, 2H), 4.06 (s, 6H), 3.32 (dt, J=14.0, 7.0 Hz, 2H), 3.06 (br d, J=7.0 Hz, 6H), 2.92 (br s, 2H), 2.52-2.49 (m, 6H), 2.14-1.88 (m, 7H), 1.68 (br s, 4H), 1.45 (br d, J=7.0 Hz, 11H), 1.38-1.17 (m, 30H).

Comparator Compound C1

1,18-bis(4-(3-isopropyl-2-(8-methoxy-[1,2,4]triazolo[1,5-a]pyridin-6-yl)-1H-indol-5-yl)piperidin-1-yl)octadecane-1,18-dione

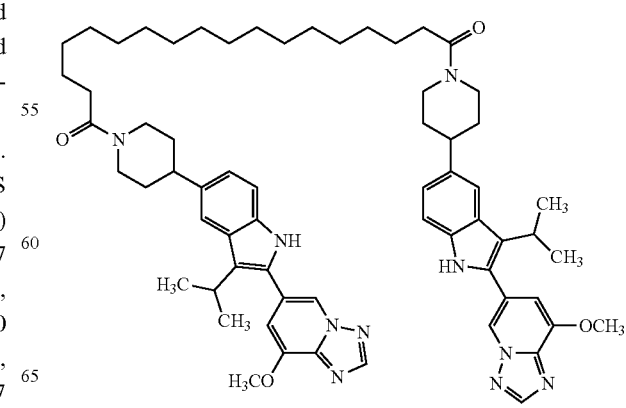

(C1)

To a mixture of octadecanedioic acid (8.88 mg, 0.028 mmol) and DIEA (0.015 mL, 0.085 mmol) in DMF (2 mL) was added HATU (21.48 mg, 0.056 mmol). After 30 minutes, 6-(3-isopropyl-5-(piperidin-4-yl)-1H-indol-2-yl)-8-methoxy-[1,2,4]triazolo[1,5-a]pyridine (22 mg, 0.056 mmol) was added. The reaction mixture was stirred for 2 hours, and then filtered and purified by HPLC to afford 1,18-bis(4-(3-isopropyl-2-(8-methoxy-[1,2,4]triazolo[1,5-a]pyridin-6-yl)-1H-indol-5-yl)piperidin-1-yl)octadecane-1,18-dione (10.6 mg, 10.02 μmol, 35.5% yield). LCMS retention time 3.02 min [QC-ACN-AA-XB]. MS (E$^+$) m/z: 1057.94 (M+H). $^1$H NMR (500 MHz, DMSO-d$_6$) δ 11.15 (s, 2H), 8.56 (s, 2H), 8.51 (s, 2H), 7.57 (s, 2H), 7.32 (d, J=8.2 Hz, 2H), 7.15 (s, 2H), 7.03 (br d, J=8.5 Hz, 2H), 4.59 (br d, J=11.9 Hz, 2H), 4.08 (s, 6H), 3.12 (br t, J=11.9 Hz, 2H), 2.85 (br t, J=12.2 Hz, 2H), 2.61 (br t, J=11.6 Hz, 2H), 2.46-2.18 (m, 5H), 1.85 (br t, J=15.3 Hz, 4H), 1.70-1.57 (m, 2H), 1.56-1.48 (m, 6H), 1.46 (br d, J=7.0 Hz, 12H), 1.36-1.20 (m, 27H).

The following compounds were prepared according to the general procedures described in the above compound.

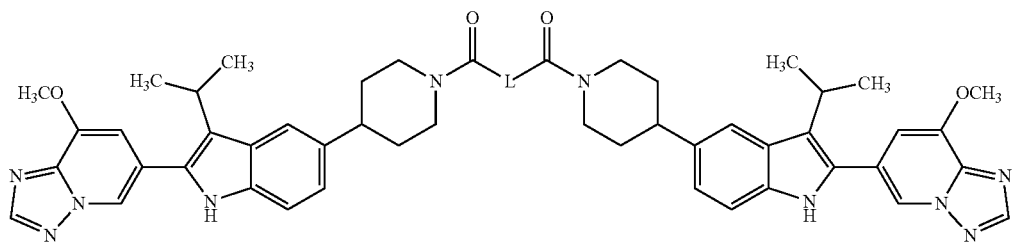

TABLE 2

| Comp No. | L | Mol. Wt. | LCMS M$^+$ | Ret Time (min) | HPLC Method |
|---|---|---|---|---|---|
| C2 | —(CH$_2$)$_{18}$— | 1085.5 | 1085.99 | 3.18 | QC-ACN-AA-XB |
| C3 | —(CH$_2$)$_{17}$— | 1071.5 | 1072.0 | 3.10 | QC-ACN-AA-XB |

Comparator Compound C4

2-(4-(3-isopropyl-2-(8-methoxy-[1,2,4]triazolo[1,5-a]pyridin-6-yl)-1H-indol-5-yl) piperidin-1-yl)ethan-1-amine

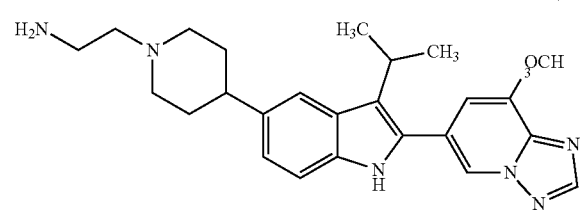

The preparation of Comparator Compound C4 is described in Intermediate 1A.

Comparator Compound C5

N-(2-(4-(3-isopropyl-2-(8-methoxy-[1,2,4]triazolo[1,5-a]pyridin-6-yl)-1H-indol-5-yl) piperidin-1-yl) ethyl)acetamide

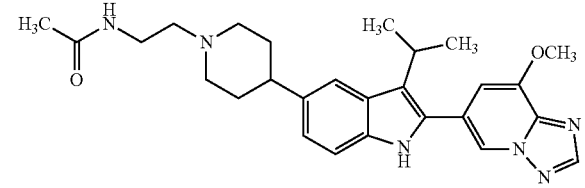

To a mixture of 2-(4-(3-isopropyl-2-(8-methoxy-[1,2,4]triazolo[1,5-a]pyridin-6-yl)-1H-indol-5-yl)piperidin-1-yl)ethan-1-amine, 2 TFA (20 mg, 0.030 mmol) and TEA (0.013 mL, 0.091 mmol) in DCM (1 mL) was added acetic anhydride (2.86 μL, 0.030 mmol). The reaction mixture was stirred for one hour, then solvents were removed in vacuo and the crude material was purified by HPLC to afford N-(2-(4-(3-isopropyl-2-(8-methoxy-[1,2,4]triazolo[1,5-a]pyridin-6-yl)-1H-indol-5-yl)piperidin-1-yl)ethyl)acetamide (12.6 mg, 0.026 mmol, 87% yield). LCMS retention time 1.16 min [QC-ACN-AA-XB]. MS (E$^+$) m/z: 475.1 (M+H). $^1$H NMR (500 MHz, DMSO-d$_6$) δ 11.14 (s, 1H), 8.56 (s, 1H), 8.52 (s, 1H), 7.81 (br s, 1H), 7.58 (s, 1H), 7.33 (d, J=8.2 Hz, 1H), 7.16 (s, 1H), 7.05 (br d, J=8.9 Hz, 1H), 4.09 (s, 3H), 3.27-3.17 (m, 1H), 3.03 (br d, J=10.7 Hz, 1H), 2.65-2.56 (m, 2H), 2.48-2.36 (m, 2H), 2.14 (br t, J=8.2 Hz, 2H), 1.92 (s, 3H), 1.87-1.69 (m, 6H), 1.47 (d, J=7.0 Hz, 6H).

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment at room temperature, the cells are then stimulated with a TLR7 ligand (gardiquimod at a final concentration of 7.5 μM), TLR8 ligand (R848 at a final concentration of 15.9 μM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

TABLE 2

TLR7/8/9 Reporter Assay Data

| Ex. No. | TLR7 $IC_{50}$ (nM) | TLR8 $IC_{50}$ (nM) | TLR9 $IC_{50}$ (nM) |
|---|---|---|---|
| 1 | 0.92 | 1.4 | 121 |
| 2 | 1.9 | 1.6 | 149 |
| 3 | 0.31 | 0.32 | 99 |
| 4 | 0.25 | 0.22 | 94 |
| 5 | 0.15 | 0.18 | 140 |
| 6 | 0.17 | 0.20 | 148 |
| 7 | 0.14 | 0.24 | 98 |
| 8 | 0.19 | 0.28 | 175 |
| 9 | 0.19 | 0.59 | 348 |
| 10 | 1.3 | 1.1 | 44 |
| 11 | 17 | 143 | 4604 |
| 12 | 191 | 509 | 13411 |
| C1 | >3125 | 3125 | >50000 |
| C3 | >3125 | >3125 | >50000 |
| C4 | 0.6 | 2.1 | 1975 |
| C5 | 0.95 | 1.8 | 3568 |

What is claimed is:

1. A compound of Formula (I)

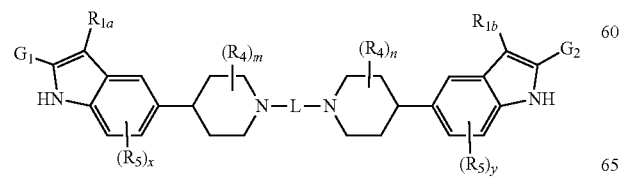

(I)

or N-oxide or a salt thereof, wherein:

L is $-(CH_2)_q-$ or $-L_1-NR_xC(O)-(CH_2)_t-C(O)NR_x-L_2-$;

$L_1$ and $L_2$ are independently $-(CH_2)_{1-3}-$;

q is an integer in the range of 10 to 30;

t is an integer in the range of 2 to 24;

$G_1$ and $G_2$ are independently:

(i)
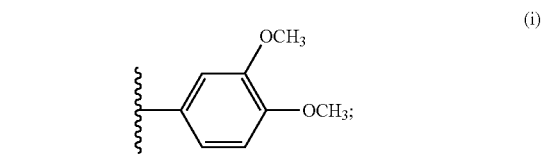

(ii)
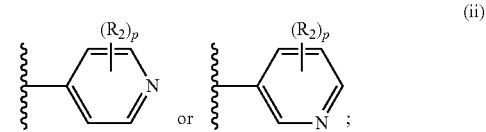

(iii)
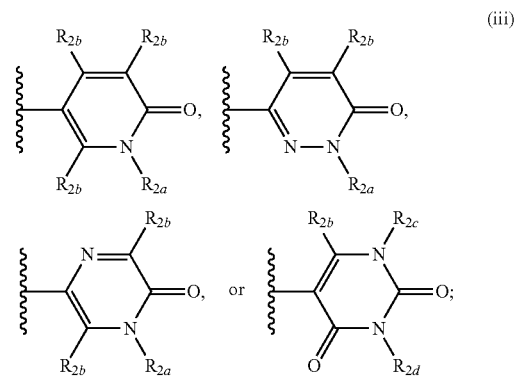

(iv) a 9-membered heterocyclic ring selected from:

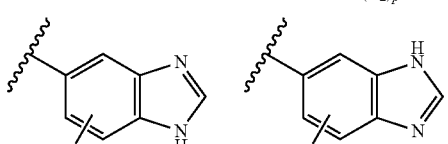

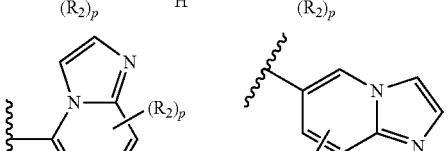

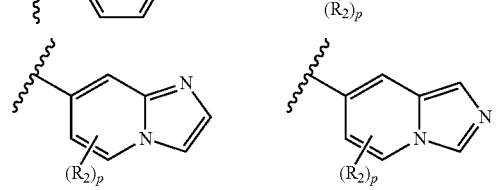

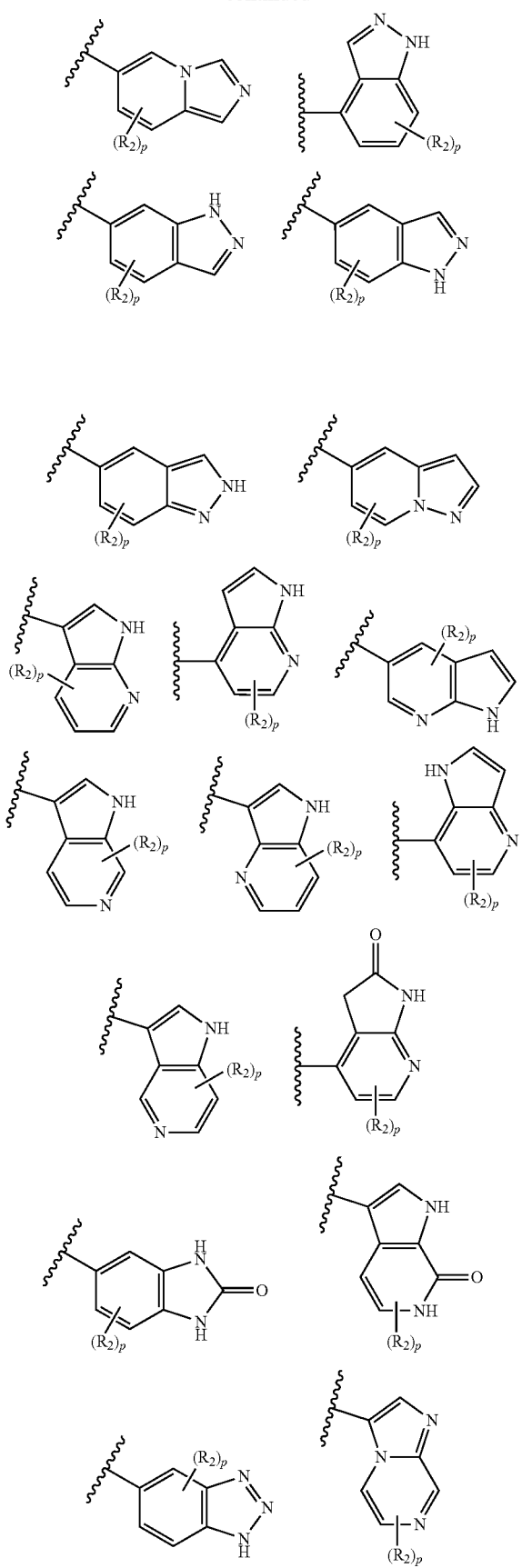
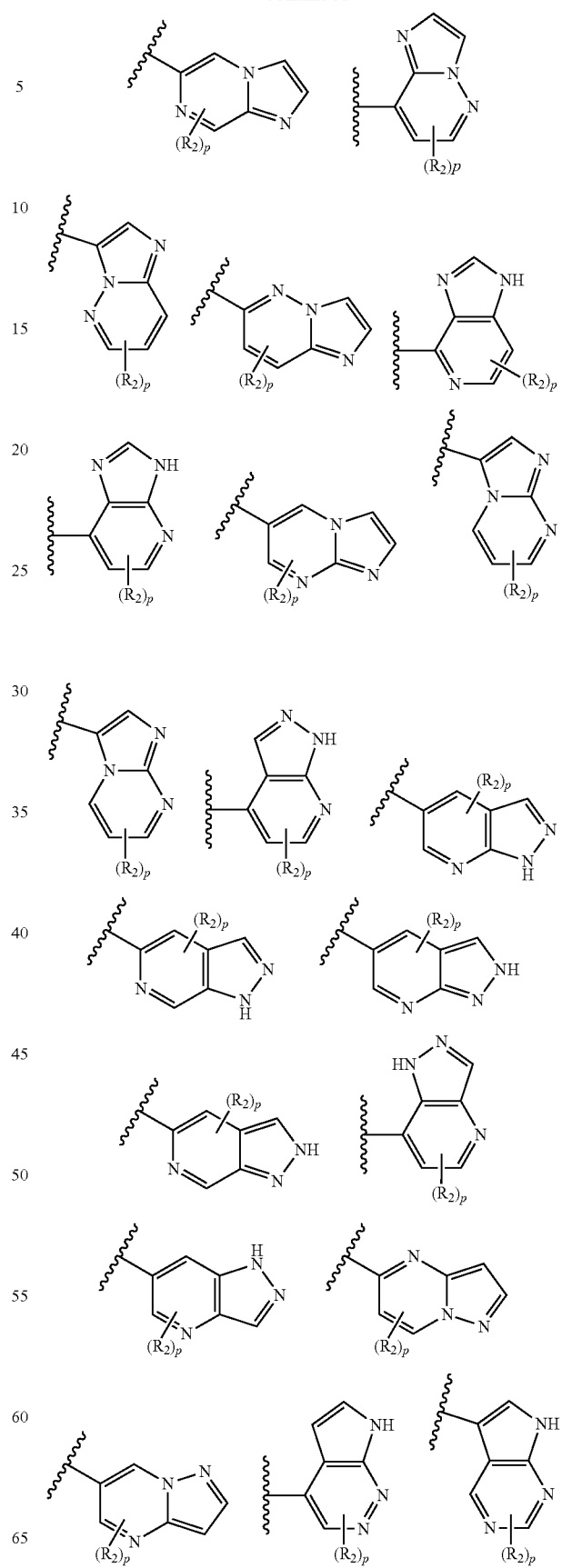

-continued
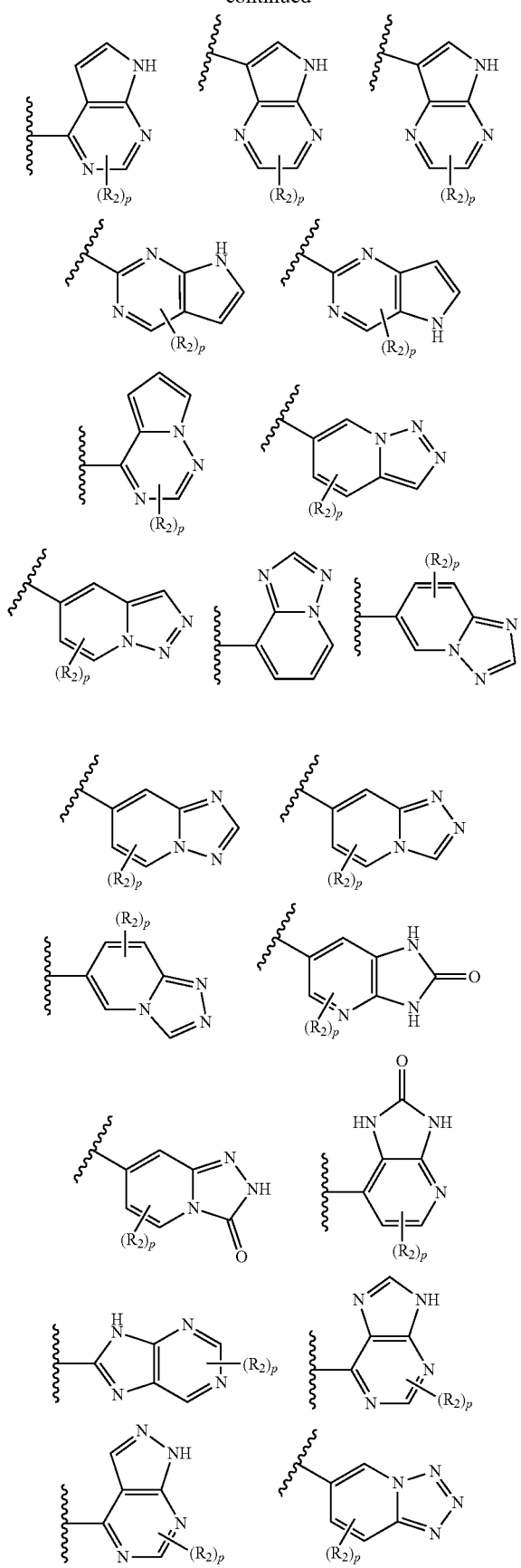
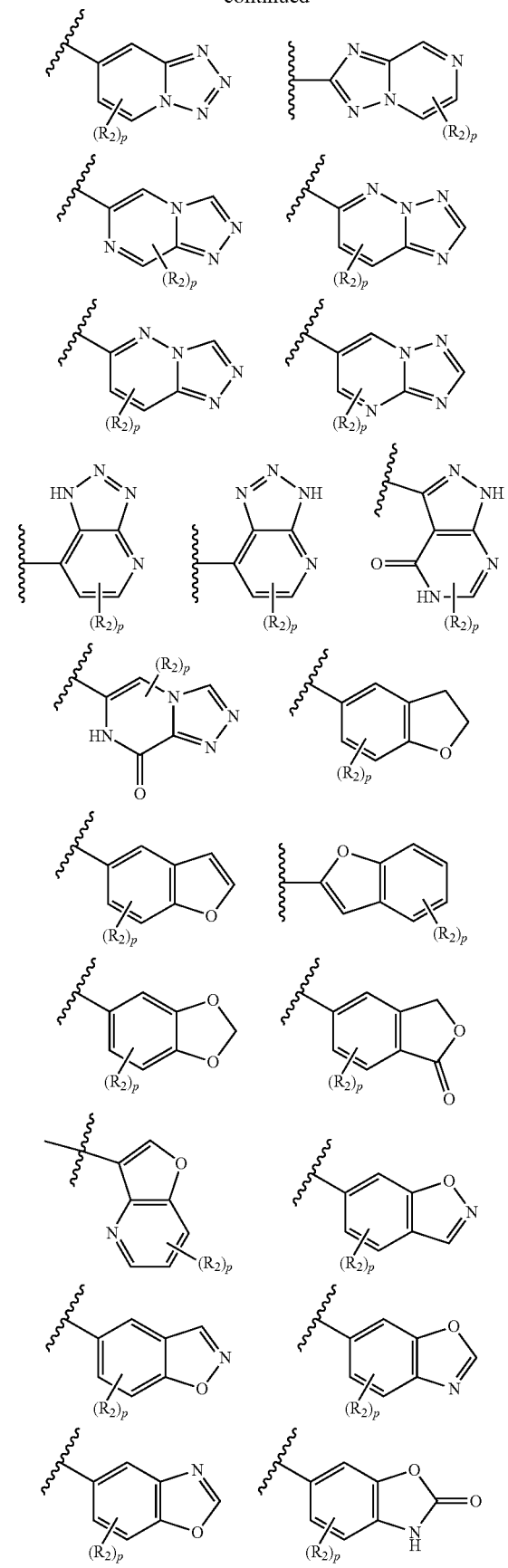

-continued or (v) 10-membered heterocyclic ring selected from:

-continued $R_{1a}$ and $R_{1b}$ are independently H, Cl, —CN, $C_{1-4}$ alkyl, $C_{1-3}$ fluoroalkyl, $C_{1-3}$ hydroxyalkyl, hydroxy-fluoroalkyl, $C_{3-6}$ cycloalkyl, —CH$_2$($C_{3-6}$ cycloalkyl), —C(O)O($C_{1-3}$ alkyl), or tetrahydropyranyl;

each $R_2$ is independently halo, —CN, —OH, —NO$_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —O(CH$_2$)$_{1-2}$OH, —(CH$_2$)$_{0-4}$O ($C_{1-4}$ alkyl), $C_{1-3}$ fluoroalkoxy, —(CH$_2$)$_{1-4}$O($C_{1-3}$ alkyl), —O(CH$_2$)$_{1-2}$OC(O)($C_{1-3}$ alkyl), —O(CH$_2$)$_{1-2}$NR$_x$R$_x$, —C(O)O($C_{1-3}$ alkyl), —(CH$_2$)$_{0-2}$C(O)NR$_y$R$_y$, —C(O)NR$_4$C$_{1-5}$ hydroxyalkyl, —C(O)NR$_x$(C$_{2-6}$ alkoxyalkyl), —C(O)NR$_x$(C$_{3-6}$ cycloalkyl), —NR$_y$R$_y$, —NR$_y$(C$_{1-3}$ fluoroalkyl), —NR$_y$(C$_{1-4}$ hydroxyalkyl), —NR$_x$H$_2$(phenyl), —NR$_x$S(O)$_2$(C$_{3-6}$ cycloalkyl), —NR$_x$(O)(C$_{1-3}$ alkyl), —NR$_x$H$_2$(C$_{3-6}$ cycloalkyl), —(CH$_2$)$_{0-2}$S(O)$_2$(C$_{1-3}$ alkyl), —(CH$_2$)$_{0-2}$(C$_{3-6}$ cycloalkyl), —(CH$_2$)$_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, —(CH$_2$)$_{0-4}$O(C$_{1-3}$ alkyl), $C_{3-6}$ cycloalkyl, —(CH$_2$)$_{1-3}$C(O)NR$_x$R$_x$, —CH$_2$(C$_{3-6}$ cycloalkyl), —CH$_2$(phenyl), tetrahydrofuranyl, tetrahydropyranyl, or phenyl;

each $R_{2b}$ is independently H, halo, —CN, —NR$_x$R$_x$, $C_{1-6}$ alkyl, $C_{1-3}$ fluoroalkyl, $C_{1-3}$ hydroxyalkyl, $C_{1-3}$ fluoroalkoxy, —(CH$_2$)$_{0-2}$O(C$_{1-3}$ alkyl), —(CH$_2$)$_{0-3}$C(O)NR$_x$R$_x$, —(CH$_2$)$_{1-3}$(C$_{3-6}$ cycloalkyl), —C(O)O(C$_{1-3}$ alkyl), —C(O)NR$_4$C$_{1-3}$ alkyl), —CR$_x$=CR$_x$R$_x$, or —CR$_x$=CH(C$_{3-6}$ cycloalkyl);

$R_{2c}$ is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_2$ is $R_{2b}$;

each $R_4$ is independently F, —OH, $C_{1-2}$ alkyl, or —OCH$_3$; or two $R_4$ attached to the same carbon atom form =O; or wherein when m or n is at least 2, two $R_4$, each attached to a different carbon atom adjacent to the nitrogen atom in a piperidinyl ring, can form a —CH$_2$CH$_2$— bridge;

each $R_5$ is independently F, Cl, —CN, $C_{1-3}$ alkyl, $C_{1-2}$ fluoroalkyl, or —OCH$_3$;

each $R_x$ is independently H or —CH$_3$;

each $R_y$ is independently H or $C_{1-6}$ alkyl;

m is zero, 1, 2, 3, or 4;

n is zero, 1, 2, 3, or 4;

each p is independently zero, 1, 2, 3, or 4;

x is zero, 1, or 2; and y is zero, 1, or 2.

2. The compound according to claim 1, or N-oxide or a salt thereof, wherein:

each of $G_1$ and $G_2$ is independently:

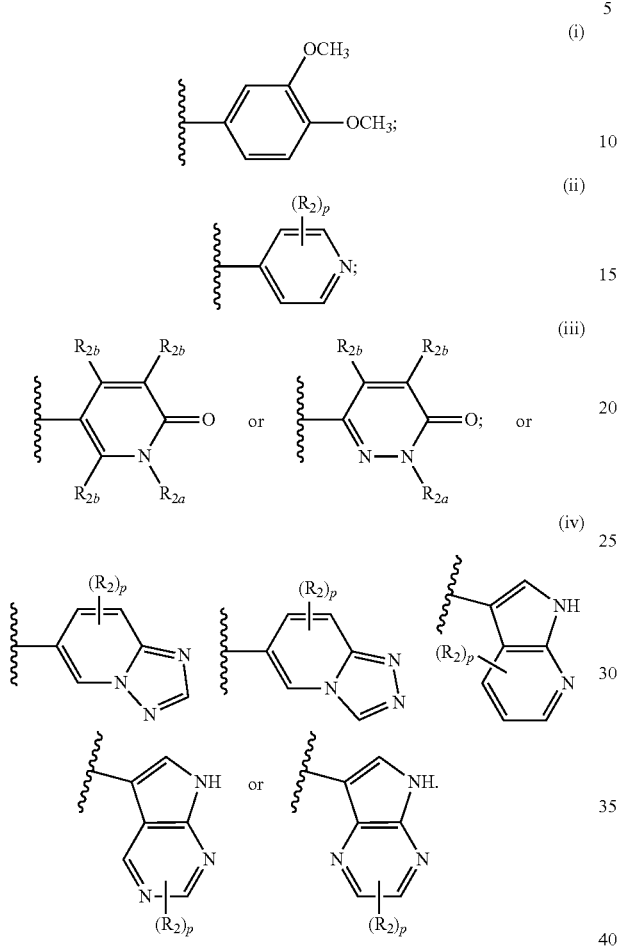

3. The compound according to claim 1, or N-oxide or a salt thereof, wherein:
q is an integer in the range of 12 to 24; and
t is an integer in the range of 2 to 20.

4. The compound according to claim 1, or N-oxide or a salt thereof, wherein:
$R_{1a}$ and $R_{1b}$ are independently H, Cl, —CN, $C_{1-4}$ alkyl, $C_{1-2}$ fluoroalkyl, $C_{1-2}$ hydroxyalkyl, or —C(O)O($C_{1-2}$ alkyl);
each $R_2$ is independently F, Cl, —CN, —OH, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, $C_{1-4}$ alkoxy, —$NR_yR_y$, —C(O)$NR_yR_y$, —C(O)$NR_x$($C_{1-4}$ hydroxyalkyl), —C(O)$NR_x$($C_{2-4}$ alkoxyalkyl), —C(O)$NR_x$($C_{3-6}$ cycloalkyl), —S(O)$_2$($C_{1-3}$ alkyl), $C_{3-6}$ cycloalkyl, morpholinyl, phenyl, or dimethyl pyrazolyl;
each $R_4$ is independently F, —$CH_3$, or —$OCH_3$;
each $R_5$ is independently F, Cl, —CN, $C_{1-2}$ alkyl, or —$OCH_3$;
m is zero, 1, or 2;
n is zero, 1, or 2;
p is zero, 1, or 2;
x is zero, or 1; and
y is zero, or 1.

5. The compound according to claim 1, or N-oxide or a salt thereof, wherein:

$R_{1a}$ and $R_{1b}$ are independently —$CH_2CH_3$ or —CH($CH_3$)$_2$;
each $R_2$ is independently —$CH_3$ or —$OCH_3$;
each $R_{2a}$ is —$CH_3$;
each $R_{2b}$ is independently H, Cl, or —$CH_3$;
each $R_4$ is independently F, —$CH_3$, or —$OCH_3$; and
each $R_5$ is independently F, Cl, —CN, —$CH_3$, —$CF_3$, or —$OCH_3$.

6. The compound according to claim 1 or a salt thereof, wherein:

$G_1$ and $G_2$ are each

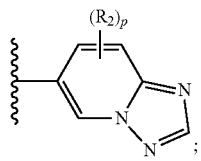

$R_{1a}$ and $R_{1b}$ are each —CH($CH_3$)$_2$;
each $R_2$ is —$OCH_3$;
L is —($CH_2$)$_{18}$— or -$L_1$-$NR_x$(O)—($CH_2$)$_t$—C(O)$NR_x$-$L_2$-;
$L_1$ and $L_2$ are each —($CH_2$)$_2$—;
t is an integer in the range of 2 to 12;
m is zero;
n is zero;
each p is 1;
x is zero; and
y is zero.

7. The compound according to claim 1 or a salt thereof, wherein said compound is:

N1,N13-bis(2-(4-(3-isopropyl-2-(8-methoxy-[1,2,4]triazolo[1,5-a]pyridin-6-yl)-1H-indol-5-yl)piperidin-1-yl)ethyl)tridecanediamide (1);

N1,N14-bis(2-(4-(3-isopropyl-2-(8-methoxy-[1,2,4]triazolo[1,5-a]pyridin-6-yl)-1H-indol-5-yl)piperidin-1-yl)ethyl)tetradecanediamine (2);

N1,N12-bis(2-(4-(3-isopropyl-2-(8-methoxy-[1,2,4]triazolo[1,5-a]pyridin-6-yl)-1H-indol-5-yl)piperidin-1-yl)ethyl)dodecanediamide (3);

N1,N11-bis(2-(4-(3-isopropyl-2-(8-methoxy-[1,2,4]triazolo[1,5-a]pyridin-6-yl)-1H-indol-5-yl)piperidin-1-yl)ethyl)undecanediamide (4);

N1,N9-bis(2-(4-(3-isopropyl-2-(8-methoxy-[1,2,4]triazolo[1,5-a]pyridin-6-yl)-1H-indol-5-yl)piperidin-1-yl)ethyl)nonanediamide (5);

N1,N8-bis(2-(4-(3-isopropyl-2-(8-methoxy-[1,2,4]triazolo[1,5-a]pyridin-6-yl)-1H-indol-5-yl)piperidin-1-yl)ethyl)octanediamide (6);

N1,N10-bis(2-(4-(3-isopropyl-2-(8-methoxy-[1,2,4]triazolo[1,5-a]pyridin-6-yl)-1H-indol-5-yl)piperidin-1-yl)ethyl)decanediamide (7);

N1,N7-bis(2-(4-(3-isopropyl-2-(8-methoxy-[1,2,4]triazolo[1,5-a]pyridin-6-yl)-1H-indol-5-yl)piperidin-1-yl)ethyl)heptanediamide (8);

N1,N6-bis(2-(4-(3-isopropyl-2-(8-methoxy-[1,2,4]triazolo[1,5-a]pyridin-6-yl)-1H-indol-5-yl)piperidin-1-yl)ethyl)adipamide (9);

N1,N12-bis(2-(4-(3-isopropyl-2-(8-methoxy-[1,2,4]triazolo[1,5-a]pyridin-6-yl)-1H-indol-5-yl)piperidin-1-yl)ethyl)dodecanediamide (10);

N1,N4-bis(2-(4-(3-isopropyl-2-(8-methoxy-[1,2,4]triazolo[1,5-a]pyridin-6-yl)-1H-indol-5-yl)piperidin-1-yl)ethyl)succinamide (11); or 1,18-bis(4-(3-isopropyl-2-(8-methoxy-[1,2,4]triazolo[1,5-a]pyridin-6-yl)-1H-indol-5-yl)piperidin-1-yl)octadecane (12).

8. A pharmaceutical composition comprising a compound according to claim 1 or a pharmaceutically-acceptable salt thereof; and a pharmaceutically acceptable carrier.

* * * * *